United States Patent
Matkovich et al.

(10) Patent No.: US 6,655,655 B1
(45) Date of Patent: Dec. 2, 2003

(54) CONNECTOR ASSEMBLIES, FLUID SYSTEMS, AND METHODS FOR MAKING A CONNECTION

(75) Inventors: Vlado Ivan Matkovich, Glen Cove, NY (US); Thomas J. Bormann, Melville, NY (US); Gerard R. Delgiacco, Yonkers, NY (US); Mladen Franovic, Cos Cob, CT (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 09/423,374
(22) PCT Filed: May 8, 1998
(86) PCT No.: PCT/US98/09653
§ 371 (c)(1),
(2), (4) Date: Jun. 26, 2000
(87) PCT Pub. No.: WO98/50105
PCT Pub. Date: Nov. 12, 1998

Related U.S. Application Data

(60) Provisional application No. 60/046,051, filed on May 9, 1997.

(51) Int. Cl.⁷ ................................................. F16L 37/28
(52) U.S. Cl. ..................... 251/149.1; 604/256; 604/905
(58) Field of Search ................................. 604/256, 905; 251/149.1

(56) References Cited

U.S. PATENT DOCUMENTS

| | | |
|---|---|---|
| 3,685,795 A | 8/1972 | Caster |
| 3,784,235 A | 1/1974 | Kessler et al. |
| 3,890,971 A | 6/1975 | Leeson et al. |
| 3,902,489 A | 9/1975 | Carter |
| 3,968,195 A | 7/1976 | Bishop |

(List continued on next page.)

FOREIGN PATENT DOCUMENTS

| | | |
|---|---|---|
| CH | 677964 | 7/1991 |
| DE | 1929522 | 12/1970 |
| DE | 3210964 | 10/1983 |
| EP | 256640 | 2/1988 |
| EP | 545598 | 6/1993 |
| EP | 0639 389 A1 | 8/1994 |
| FR | 1322012 | 2/1963 |
| FR | 1380396 | 10/1964 |
| FR | 2097975 | 3/1972 |
| FR | 2606643 | 5/1988 |
| FR | 2608250 | 6/1988 |
| FR | 2614386 | 10/1988 |
| GB | 1132443 | 10/1968 |
| GB | 2008705 | 6/1979 |
| WO | 83/03538 | 10/1983 |
| WO | 89/00432 | 1/1989 |
| WO | 92/19314 | 11/1992 |
| WO | 94/08173 | 4/1994 |
| WO | 96/30076 | 10/1996 |

*Primary Examiner*—A. Michael Chambers
(74) *Attorney, Agent, or Firm*—Leydig, Voit & Mayer, Ltd.

(57) ABSTRACT

A connector assembly and a fluid system or device comprise a connector assembly which includes first and second fittings, each fitting having an aperture, and a stem disposed in the aperture of the first fitting. In various embodiments of the invention, the connector assembly may further comprise a socket cooperatively arranged with one of the first and second fittings, at least one resilient sealing member, a sealing layer joined to the socket or covering the resilient sealing member, and/or a deformable locking device. A method for making a connection includes mating a first fitting having an aperture and a second fitting having an aperture without fluid within the first and second fittings, establishing a fluid flowpath through the first and second fittings by advancing a stem having a head through the aperture of the first fitting into the aperture of the second fitting, and establishing fluid flow through the first and second fittings by opening a fluid blocking mechanism.

29 Claims, 17 Drawing Sheets

U.S. PATENT DOCUMENTS

| | | |
|---|---|---|
| 3,986,508 A | 10/1976 | Barrington |
| 4,019,512 A | 4/1977 | Tenczar |
| 4,022,205 A | 5/1977 | Tenczar |
| 4,022,496 A | 5/1977 | Crissy et al. |
| 4,030,494 A | 6/1977 | Tenczar |
| 4,048,997 A * | 9/1977 | Raghavachari et al. ..... 604/189 |
| 4,080,965 A | 3/1978 | Phillips |
| 4,161,949 A | 7/1979 | Thanawalla |
| 4,191,225 A | 3/1980 | Ogle |
| 4,195,632 A | 4/1980 | Parker et al. |
| 4,201,208 A | 5/1980 | Cambio, Jr. |
| 4,256,106 A | 3/1981 | Shoor |
| 4,265,280 A | 5/1981 | Ammann et al. |
| 4,289,337 A | 9/1981 | Roe |
| 4,334,551 A | 6/1982 | Pfister |
| 4,336,802 A | 6/1982 | Stone et al. |
| 4,368,729 A | 1/1983 | Dossin |
| 4,410,321 A | 10/1983 | Pearson et al. |
| 4,418,945 A | 12/1983 | Kellogg |
| 4,432,755 A | 2/1984 | Pearson |
| 4,443,215 A | 4/1984 | Smith |
| 4,457,749 A | 7/1984 | Bellotti et al. |
| 4,488,961 A | 12/1984 | Spencer |
| 4,507,119 A | 3/1985 | Spencer |
| 4,508,367 A | 4/1985 | Oreopoulos et al. |
| 4,511,359 A | 4/1985 | Vaillancourt |
| 4,512,766 A | 4/1985 | Vailancourt |
| 4,516,971 A | 5/1985 | Spencer |
| 4,521,263 A | 6/1985 | Benin et al. |
| 4,531,768 A | 7/1985 | Summers |
| 4,564,054 A | 1/1986 | Gustavsson |
| 4,573,978 A | 3/1986 | Reilly |
| 4,591,049 A * | 5/1986 | Walter et al. ............... 206/222 |
| 4,610,469 A | 9/1986 | Wolff-Mooij |
| 4,610,670 A | 9/1986 | Spencer |
| 4,617,012 A | 10/1986 | Vaillancourt |
| 4,619,642 A | 10/1986 | Spencer |
| 4,636,204 A | 1/1987 | Christopherson et al. |
| 4,680,025 A | 7/1987 | Kruger et al. |
| 4,737,214 A | 4/1988 | Leurink et al. |
| 4,752,292 A | 6/1988 | Lopez et al. |
| 4,753,697 A | 6/1988 | Shaposka et al. |
| 4,767,400 A | 8/1988 | Miller et al. |
| 4,768,568 A | 9/1988 | Fournier et al. |
| 4,770,735 A | 9/1988 | Shaposka et al. |
| 4,792,163 A | 12/1988 | Kulle |
| 4,793,880 A | 12/1988 | Shaposka et al. |
| 4,798,605 A | 1/1989 | Steiner et al. |
| 4,816,221 A | 3/1989 | Harvey et al. |
| 4,828,557 A | 5/1989 | Persidsky |
| 4,832,773 A | 5/1989 | Shaposka et al. |
| 4,838,875 A | 6/1989 | Somor |
| 4,840,690 A | 6/1989 | Melinyshyn et al. |
| 4,843,017 A | 6/1989 | Oberhardt et al. |
| 4,844,512 A | 7/1989 | Gahwiler |
| 4,864,101 A | 9/1989 | Shaposka et al. |
| 4,897,138 A | 1/1990 | Shaposka et al. |
| 4,913,756 A | 4/1990 | Shaposka et al. |
| 4,933,036 A | 6/1990 | Shaposka et al. |
| 4,941,517 A | 7/1990 | Galloway |
| 4,944,728 A | 7/1990 | Carrell et al. |
| 4,950,260 A | 8/1990 | Bonaldo |
| 4,978,446 A | 12/1990 | Lobdell |
| 4,991,882 A | 2/1991 | Gähwiler |
| 4,995,869 A | 2/1991 | McCarthy |
| 4,998,713 A | 3/1991 | Vaillancourt |
| 4,998,921 A | 3/1991 | Vickroy et al. |
| 4,998,927 A | 3/1991 | Vaillancourt |
| 5,017,259 A | 5/1991 | Kohsai |
| 5,065,783 A | 11/1991 | Ogle, II |
| 5,067,950 A | 11/1991 | Broadnax, Jr. |
| 5,108,380 A | 4/1992 | Herlitze et al. |
| 5,117,875 A | 6/1992 | Marrucchi |
| 5,122,123 A | 6/1992 | Vaillancourt |
| 5,122,129 A | 6/1992 | Olson et al. |
| 5,158,549 A | 10/1992 | McCarthy |
| 5,195,993 A | 3/1993 | Gianakos |
| 5,224,936 A | 7/1993 | Gallagher |
| 5,232,454 A | 8/1993 | Hollister |
| 5,250,030 A | 10/1993 | Corsich |
| 5,267,972 A | 12/1993 | Anderson |
| 5,279,583 A | 1/1994 | Shober, Jr. et al. |
| 5,279,591 A | 1/1994 | Simon |
| 5,295,972 A | 3/1994 | Mischenko |
| 5,334,180 A | 8/1994 | Adolf et al. |
| 5,374,256 A * | 12/1994 | Kriesel ....................... 604/232 |
| 5,380,049 A | 1/1995 | Smowton |
| 5,393,101 A | 2/1995 | Matkovich |
| 5,437,639 A | 8/1995 | Malenchek |
| 5,492,147 A | 2/1996 | Challender et al. |
| 5,549,568 A | 8/1996 | Shields |
| 5,628,726 A | 5/1997 | Cotter |
| 5,653,698 A | 8/1997 | Niedospial et al. |
| 5,688,254 A | 11/1997 | Lopez et al. |
| 5,738,671 A | 4/1998 | Niedospial, Jr. et al. |
| 5,749,861 A | 5/1998 | Guala et al. |
| 5,810,398 A | 9/1998 | Matkovich |
| 5,839,715 A | 11/1998 | Leinsing |
| 5,848,997 A | 12/1998 | Erskine et al. |
| 5,868,433 A | 2/1999 | Matkovich |
| 6,162,206 A | 12/2000 | Bindokas et al. |
| 6,341,802 B1 | 1/2002 | Matkovich |
| 6,394,992 B1 | 5/2002 | Sjöholm |

* cited by examiner

CONNECTOR ASSEMBLIES, FLUID SYSTEMS, AND METHODS FOR MAKING A CONNECTION

This application claims the priority of U.S. provisional patent application No. 60/046,051, filed May 9, 1997, which is incorporated by reference in its entirety.

FIELD OF THE INVENTION

The present invention relates to connector assemblies, fluid systems or devices including a connector assembly, and methods for making a connection. More particularly, the invention relates to connector assemblies and fluid systems or devices, which maintain the sterility of a fluid which passes through them, and methods for making a sterile connection.

BACKGROUND OF THE INVENTION

Connector assemblies have been developed to handle fluids e.g., biological fluids, while preserving their condition. More particularly, connectors have been developed to preserve the condition of a fluid, or maintain a fluid free of contaminants. Freedom from contaminants refers to a relative amount of contaminants and is variously defined according to a specific industry, fluid and/or intended use. For example, a biological fluid is considered free of contaminants if it is substantially free of viable microorganisms and is typically referred to as "sterile". Connector assemblies for use with biological fluids, for example, have been fashioned to preserve sterility of the fluid.

Attempts have been made to develop connector assemblies which isolate a fluid from the ambient environment of the connector, and from contaminants entrained in the ambient environment. Such connectors typically define a fluid conduit, the interior of which is isolated from the ambient environment. Some conventional connector assemblies include mating male and female connectors having opposing surfaces and a removable protective cover on each opposing surface to be contacted. These covers must be removed prior to actually coupling the connectors.

A problem associated with these conventional connector assemblies in which protective covers must be removed prior to coupling is that removing the covers may not sufficiently protect the fluid flowing through these assemblies. To unfasten and remove a cover, a technician must manually manipulate the removable cover in intimate proximity to the protected region under the cover, risking incidental contact and the transmission of contaminants to the protected region.

In addition, once the protective covers are removed from the protected surfaces, the protected regions are exposed to the contaminant-laden ambient environment. For example, as the connectors are brought together, dust, microorganisms, and other airborne contaminants may contact the protected regions, even if the connectors are quickly mated. Thus, while these conventional connector assemblies have been developed to form a sterile connection. none adequately protect the fluid flowing through the connector assembly.

Another type of conventional connector assembly comprises mating male and female fittings, each fitting having a protective cover attached to a connecting end of the fitting, and a piercing member inside the male fitting to pierce the protective covers and join the interiors of the mating fittings. One problem with these fittings is that the piercing member may prematurely pierce the cover before the fittings are coupled together. As a result, contaminants may enter the connector and it must either be resterilized or discarded.

Another problem which may occur with conventional connector assemblies including piercing members is that the piercing member may sever a portion of one or both of the covers between the connecting ends of the male and female fittings when the fittings are coupled together. The severed portion of the membrane may enter a fluid flow path defined by the interior region of the fittings and contaminate the system or interfere with the flow of fluid through the connector.

Another problem that exists with conventional connector assemblies is obtaining a good seal between the male and female fittings. When the protective covers covering the connecting ends are removed and the connecting ends of male and female fittings are joined, there may be gaps between the joined connecting ends due to unmatched surfaces. The gaps may allow contaminants to enter and compromise the sterility of the inner region of the fittings. Thus, there exists a need for a sterile connector assembly which provides a good seal between opposing connecting ends of the male and female fittings.

Another problem associated with conventional connectors having protective covers is that, prior to assembly of the connectors, the protective covers are exposed. Consequently, when the connectors are handled, the protective covers may be easily damaged or punctured, or accidentally or inadvertently removed. As a result, the contaminants may enter the connectors, and the connectors must be discarded. In some cases, the damages to the protective covers may not be easily discovered, and contaminated connectors may be unknowingly used and the fluid flowing through the connector assembly may be contaminated.

SUMMARY OF THE INVENTION

Various aspects of the present invention overcome many of the problems associated with the conventional connector assemblies, including many of the problems previously outlined.

In accordance with one aspect of the invention, a connector assembly comprises a first fitting, a second fitting, a socket, a resilient sealing member, and a stem. The first fitting includes an aperture and the second fitting, which is capable of being coupled to the first fitting, also includes an aperture. The socket, which includes a side wall, is cooperatively arranged with the first fitting or the second fitting. The resilient sealing member is disposed in the socket. The resilient sealing member includes a first portion disposed in the socket and contacting the side wall of the socket and a second portion disposed in the socket and spaced from the side wall of the socket. The stem, which includes a head, is disposed in the first fitting. The stem is axially movable through the socket and the resilient sealing member into the aperture of the second fitting.

In accordance with another aspect of the invention, a connector assembly comprises a first fitting, a second fitting, a socket, a resilient sealing member, and a stem. The first fitting includes an aperture and the second fitting, which is capable of being coupled to the first fitting, also includes an aperture. The socket is cooperatively arranged with the first fitting or the second fitting. The resilient sealing member, which is disposed in the socket, includes a first portion, a second portion, and a third portion. The second portion is disposed between the first portion and the third portion and has a thinner wall than the first portion and the third portion. The stem, which includes a head, is disposed in the first fitting. The stem is axially movable through the socket and the resilient sealing member into the aperture of the second fitting.

In some embodiments of the invention, a connector assembly also comprises a sealing layer. The socket includes an open end, and the sealing layer is removably joined to the open end of the socket and is removable from the socket.

In some embodiments of the invention, a connector assembly also comprises a sealing layer. The socket includes a continuous cylindrical wall, and the sealing layer covers the resilient sealing member. The stem includes a distal end sealed to the first fitting and is axially movable through the first fitting, the socket, and the resilient sealing member into the aperture of the second fitting.

In some embodiments of the invention, a connector assembly also comprises a removable sealing layer. The removable sealing layer contacts the resilient sealing member.

In some embodiments of the invention, a connector assembly also comprises a deformable locking device. The stem is axially movable through the aperture of the first fitting into the aperture of the second fitting. The deformable locking device includes a bendable member arranged between the first fitting and the stem to prevent the head from moving through the aperture of the first fitting. In some embodiments of the invention, a connector assembly also comprises a first cap, a second cap, and a sealing layer. The first fitting has a proximal end the second fitting has a proximal end. The first cap is removably associated with the proximal end of the first fitting, and protects the proximal end of the first fitting. The second cap is removably associated with the proximal end of the second fitting, and protects the proximal end of the second fitting. The sealing layer is arranged to seal the aperture of one of the first and second fittings. The stem is axially movable through the aperture of the first fitting into the aperture of the second fitting.

In some embodiments of the invention, a fluid system or device comprises a connector assembly according to one or both aspects of the invention and a fluid container or conduit. The container or conduit is coupled to either one of the first and second fittings of the connector assembly.

For some embodiments of the invention, a method for making a connection comprises mating a first fitting having an aperture and a second fitting having an aperture without fluid within the first and second fittings, establishing a fluid flowpath through the first and second fittings by advancing a stem having a head through the aperture of the first fitting into the aperture of the second fitting, and establishing fluid flow through the first and second fittings by opening a fluid blocking mechanism.

For some embodiments of the invention, a method for making a connection comprises removing a cap operatively associated with a proximal end of one of a first fitting and a second fitting, each of which has an aperture, mating the first fitting and the second fitting, removing stripout layers covering respectively the apertures of the first and second fittings, and establishing a fluid flowpath through the first and second fittings by advancing a stem having a head through the aperture of the first fitting into the aperture of the second fitting.

The novel features and characteristics of this invention are set forth with particularity in the appended claims. However, the invention may best be understood with reference to the drawings, described below, and the accompanying detailed description of preferred embodiments.

In accordance with another aspect of the invention, a connector assembly comprises a first fitting, a second fitting, a resilient sealing member, and a stem. The first fitting includes an aperture and the second fitting, which is capable of being coupled to the first fitting, also includes an aperture. The socket is cooperatively arranged with the first fitting or the second fitting. The resilient sealing member, which is disposed in the socket, includes a first portion, a second portion, and a third portion. The second portion is disposed between the first portion and the third portion and has a thinner wall than the first portion and the third portion. The stem, which includes a head, is disposed in the first fitting. The stem is axially movable through the socket and the resilient sealing member into the aperture of the second fitting.

In accordance with another with another aspect of the invention, a connector assembly comprises a first fitting, a second fitting, a stem, a socket, a resilient sealing member, and a sealing layer. The first fitting has an aperture and the second fitting, which is capable of being coupled to te first fitting, also has an aperture. The stem is disposed in the first fitting. The socket, wich includes an open end is cooperatively arranged with the first fitting or the second ftting. The resilient sealing member is disposed in the socket, and the sealing layer is removably joined to the open end of the socket and is removable from the socket.

In accordance with another aspect of the invention, a connector assembly comprises a first fitting, a second fitting, a socket, a resilient sealing member, a sealing layer, and a stem. The first fitting has an aperture and the second fitting, which is capable of being coupled to The first fitting, also has an aperture. The socket, which includes a continuous cylindrical wall, is cooperatively arranged with the first fitting or the second fitting. The resilient sealing member is disposed in the socket, and the sealing layer covers the resilient sealing member. The stem, which includes a head and a distal end sealed to the first fitting is disposed in the first fitting. The stem is axially movable through the first fitting, the socket, and the resilient sealing member into the aperture of the second fitting.

In accordance with one aspect of the invention, a connector assembly comprises a first fitting, a second fitting, a socket, a resilient sealing member, and stem. The first fitting includes an aperture and the second fitting, which is capable of being coupled to the first fitting, also includes an aperture. The socket, which includes a side wall, is cooperatively arranged with the first fitting of the second fitting. The resilient sealing member is disposed in the socket. The resilient sealing member includes a first portion disposed in the socket and contacting the side wall of the socket and a second portion disposed in the socket spaced from the side wall of the socket. The stem, which includes a head, is disposed in the first fitting. The stem is axially movable through the socket and the resilient sealing member into the aperture of the second fitting.

In accordance with another aspect of the invention, a connector assembly comprises a first fitting, a second fitting, a first resilient sealing member, a second resilient sealing member, a sealing layer, and a stem. The first fitting has an aperture and the second fitting, which is coupleable to the first fitting, also has an aperture. The first resilient sealing member is coupled to the first fitting at the aperture of the first fitting, and the second resilient sealing member is coupled to the second fitting at the aperture of the second fitting. The sealing layer is disposed between the first and second resilient sealing members, and the stem is disposed in the first fitting.

In accordance with another aspect of the invention, a connector assembly comprises a first fitting, a second fitting, a resilient sealing member, a removable sealing layer, and a stem. The first fitting has an aperture and the second fitting, which is coupleable to the first fitting, also has an aperture. The resilient sealing member is coupled to one of the first fitting and the second fitting at the aperture. The removable sealing layer contacts the resilient sealing member, and the stem is disposed in the first fitting.

In accordance with another aspect of the invention, a connector assembly comprises a first fitting, a second fitting, a stem, and a deformable locking device. The first fitting has an aperture, and the second fitting, which is capable of being coupled to the first fitting, also has an aperture. The stem, which includes a head, is disposed in the first fitting. The stem is axially movable through the aperture of the first fitting into the aperture of the second fitting. The deformable locking device includes a bendable member arranged between the first fitting and the stem to prevent the head from moving through the aperture of the first fitting.

In accordance with another aspect of the invention, a connector assembly comprises first and second fittings, a first cap, a second cap, a sealing layer, and a stem. The first fitting has an aperture and a proximal end. The second fitting is coupleable to the first fitting and has an aperture and a proximal end. The first cap is removably associated with the proximal end of the first fitting, and protects the proximal end of the first fitting. The second cap is removably associated with the proximal end of the second fitting, and protects the proximal end of the second fitting. The sealing layer is arranged to seal the aperture of one of the first fitting and the second fitting. The stem includes a head, and is disposed in the first fitting and axially movable through the aperture of the first fitting into the aperture of the second fitting.

In accordance with another aspect of the invention, a fluid system or device comprises any of the previous connector assemblies and a fluid container or conduit. The container or conduit is coupled to either one of the first and second fittings of the connector assembly.

In accordance with another aspect of the invention, a method for making a connection comprises mating a first fitting having an aperture and a second fitting having an aperture without fluid within the first and second fittings, establishing a fluid flowpath through the first and second fittings by advancing a stem having a head through the aperture of the first fitting into the aperture of the second fitting, and establishing fluid flow through the first and second fittings by opening a fluid blocking mechanism.

In accordance with another aspect of the invention, a method for making a connection comprises removing a cap operatively associated with a proximal end of one of a first fitting and a second fitting, each of which has an aperture, mating the first fitting and the second fitting, removing stripout layers covering respectively the apertures of the first and second fittings, and establishing a fluid flowpath through the first and second fittings by advancing a stem having a head through the aperture of the first fitting into the aperture of the second fitting.

The novel features and characteristics of this invention are set forth with particularity in the appended claims. However, the invention may best be understood with reference to the drawings, described below, and the accompanying detailed description of preferred embodiments.

DETAILED DESCRIPTION OF THE INVENTION

Figure 1:
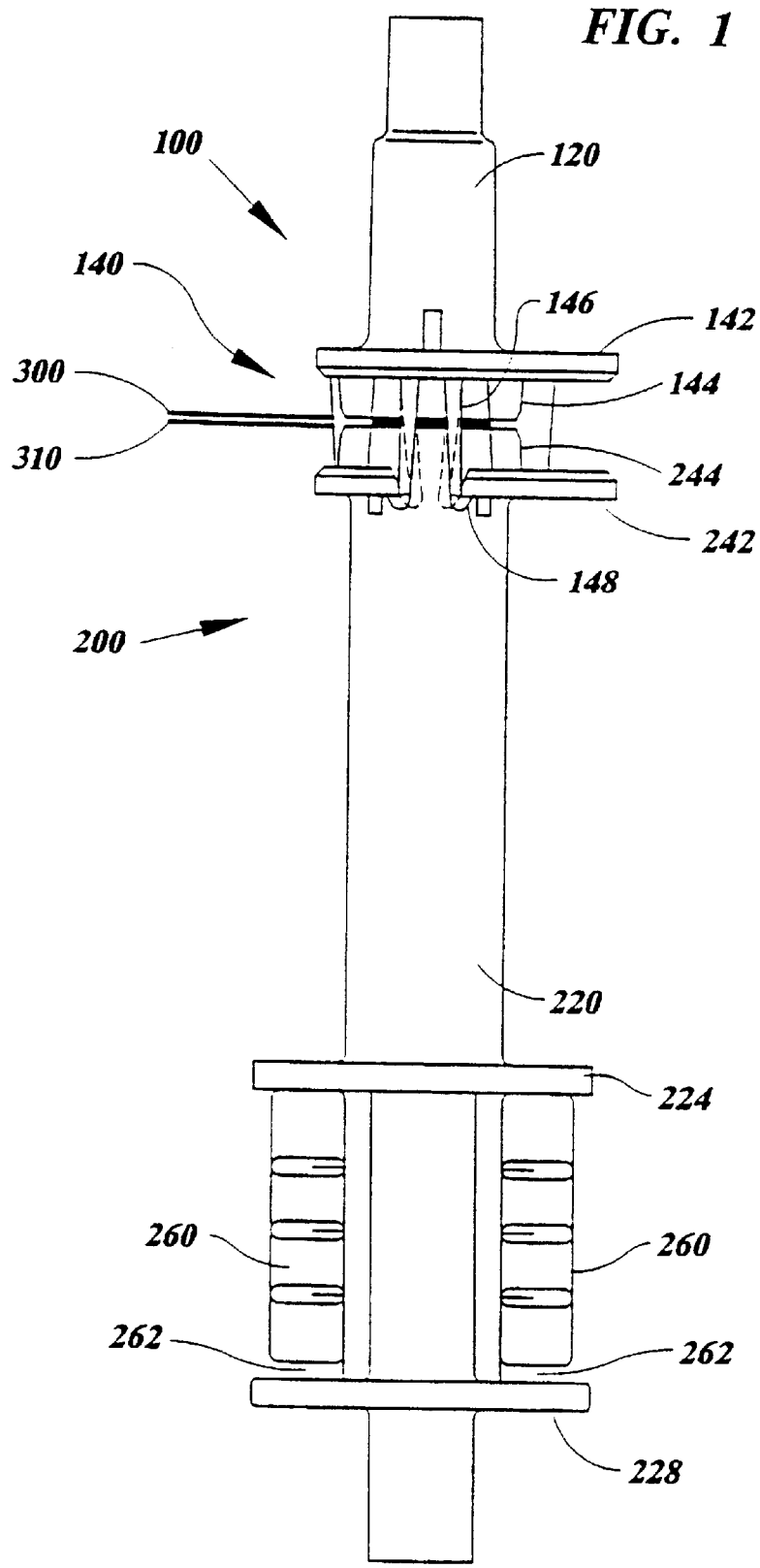
FIG. 1 is a side view of a connector assembly according to an embodiment of the present invention.

A connector assembly according to an embodiment of the present invention includes mating connectors which can be coupled to connect different fluid conduit sections defining a fluid flow path, e.g., a liquid flow path. The connector assembly isolates the fluid flow path from the ambient environment and from contaminants present in the ambient environment and is preferably sterile. Consequently, a connector assembly according to the present invention is suitable for use in an open system, a closed system, or a closed sterile system.

In an embodiment illustrated in FIGS. 1–7, the connector assembly comprises two connectors, preferably a female connector 100 and a male connector 200. Each connector may be attached to or formed as part of any suitable fluid container or conduit, for example, a section of tubing, an inlet or outlet of a housing, such as a filter housing or drip chamber housing, or a flexible bag such as a blood bag. Each connector may comprise any structure suitable for fluid communication, preferably liquid communication, e.g. a housing of any form capable of containing fluid. The exemplary female connector 100 generally comprises a fitting 120, preferably of unitary construction. An exemplary male connector 200 generally comprises a stem 210 and a fitting 220. The fittings 120, 220 of the female and male connectors 100, 200 are preferably formed from a polymeric material. For example, the fittings 120, 220 may be molded from a polymeric material such as polycarbonate or polypropylene.

For directional orientation in the following discussion, each connector has a proximal end, nearest the opposing connector, and a distal end furthest from the opposing connector. Also, since the exemplary connectors 100, 200 in FIG. 1 comprise generally elongated bodies, the term axial denotes disposition along their axes.

Figure 3:
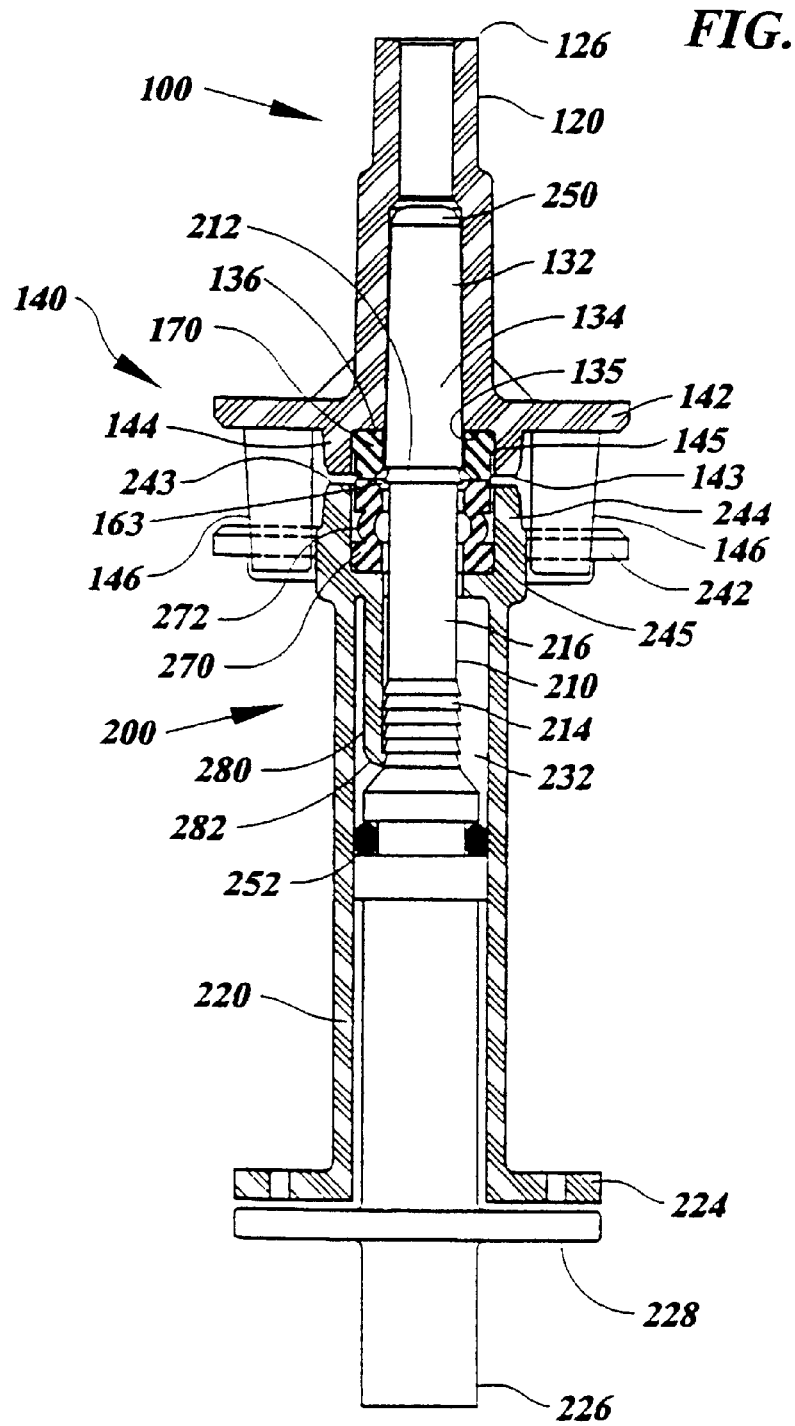
FIG. 3 is a side view in partial section of the connector assembly with the stripout layers removed and the stem inserted into the female fitting.
Figure 5:
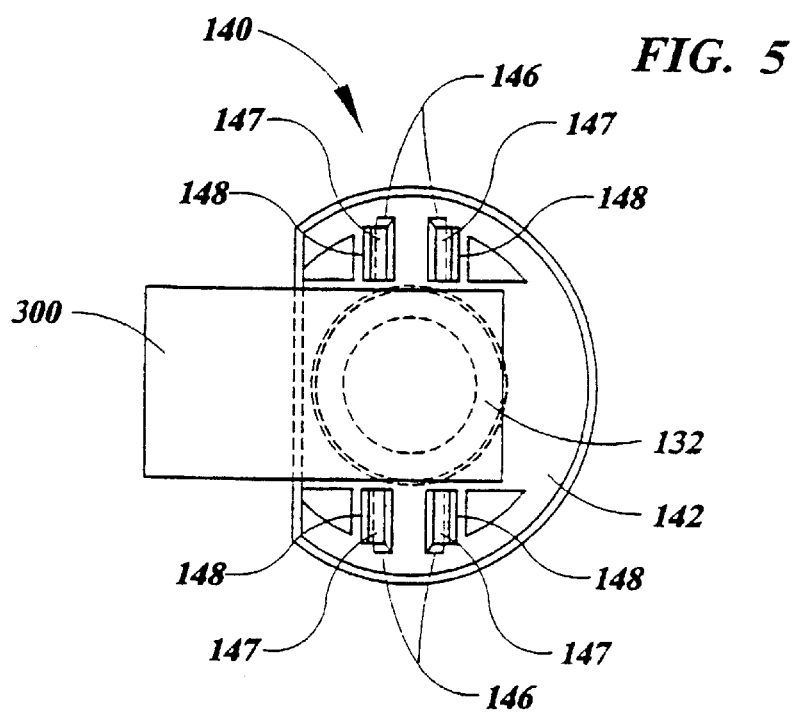
FIG. 5 is an end view of a female connector in an unconnected state.

The female and male connectors 100, 200 may also comprise an interlocking mechanism adapted to interlock the female connector 100 in predetermined relation with the male connector 200. The interlocking mechanism may have any suitable configuration, such as interlocking sleeves or threaded connections. In a preferred embodiment, the portion of the interlocking mechanism on the female fitting 120 may include a bracket 140. The bracket 140 may be variously configured. The bracket 140 may comprise a socket 145 or cup having any suitable plan form, e.g. rectangular or circular. In the illustrated embodiment, the bracket 140 comprises a generally C-shaped member. The representative bracket 140 may include a flange 142 and a generally cylindrical sidewall 144 defining a socket 145. The flange 142 may assume a radially extending annular plan form, for example, as best seen in FIG. 5. In the embodiment of FIG. 3, the sidewall 144 extends from and is concentric with the flange 142 and includes an annular proximal end surface 143 facing the male connector 200.

Figure 4:
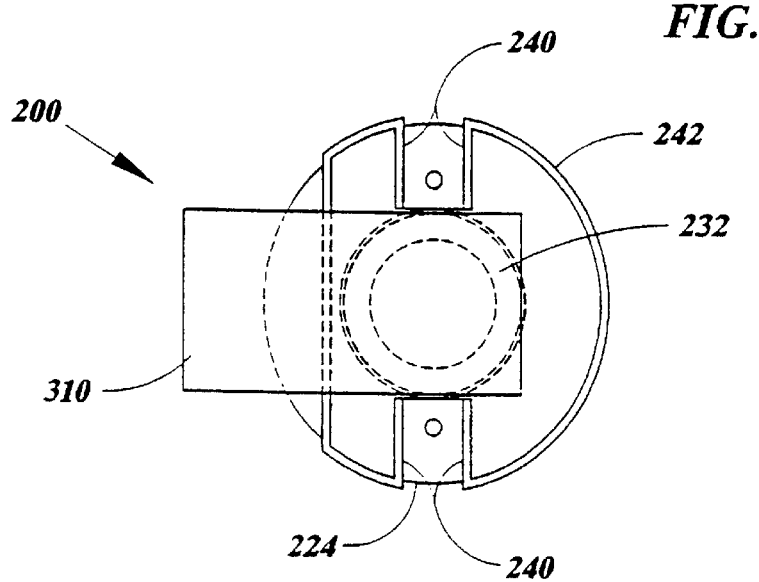
FIG. 4 is an end view of a male connector in an unconnected state.

One or more forks 146 may extend from the flange 142. The forks 146 may be formed, integrally with the flange 142. When the female connector 100 is coupled to the male connector 200, the forks 146 preferably register in slots 240 formed in an upper flange 242 of the male connector 200. While in the illustrated embodiment, the forks 146 extend from the female connector 100 and the slots 240 are in the male connector 200, the forks and slots may instead be associated with the male and female connectors, respectively. The forks 146 are best illustrated in FIG. 5. The slots 240 are best illustrated in FIG. 4. Each fork 146 preferably comprises first and second prongs 147 which are preferably flexible to allow the prongs 147 to enter and lock in the slots 240. Catches 148 can be formed on the prongs 147 of the forks 146 which pass through the slots 240 and abut a distal surface of the upper flange 242. In this manner, the forks 146 extend through the slots 240 and engage the upper flange 242 of the male connector 200 to interlock the connectors 100, 200.

The female connector 100 is preferably adapted to contain fluid and conduct fluid communication and preferably defines an isolated portion of the fluid flow path, e.g., containing or conducting isolated fluid communication. The female fitting 120 may define an internal chamber or aperture 132 which may have any suitable configuration and preferably has an open proximal end. The distal end 126 of the female fitting 120 may be connected to any suitable fluid container or conduit as best shown on FIGS. 11–14. For example, the distal end 126 of the female fitting 120 may be bonded to a section of tubing 10 or to the top, the bottom or the wall of a container using any suitable bonding technique. Alternatively, the female fitting 120 may be molded integrally with the tubing 10 or the container. The fluid conduit or container may be connected in fluid communication with the internal chamber 132 of the female fitting 120. The internal chamber 132 may comprise a bore 134 relieved at its proximal end into a counterbore 136 having a larger inner diameter than the bore 134. The cylindrical sidewall 144 surrounds the proximal end of the chamber 132 and defines the counterbore 136.

The female connector 100 preferably further comprises a sealing layer sealing the open proximal end of the aperture 132 in the female fitting 120. For example, the sealing layer preferably comprises a removable sealing layer, such as a female stripout layer 300 removably attached to the proximal end of the female fitting 120. In the illustrated embodiment, the female stripout layer 300 is attached to the open proximal end of the sidewall 144. For example, the female stripout layer 300 may be bonded to the proximal end surface 143 of the female fitting 120 through any suitable technique, for example, ultrasonic welding. The stripout sealing layer 300 preferably seals the chamber 132 of the female connector 100 from the ambient atmosphere. The female stripout sealing layer 300 preferably includes a pull tab that extends beyond the periphery of the connectors 100, 200 to allow removal when the connectors 100, 200 are joined.

The male connector 100 also preferably comprises a sealing layer which seals the open proximal end of an aperture 232 in the male fitting 220. For example, the sealing layer preferably comprises a removable sealing layer such as a male stripout layer 310 removably attached to the proximal end of the male fitting 220. In the illustrated embodiment, the male stripout layer 310 is attached to the proximal end surface 243 at the open end of a generally cylindrical sidewall 244 at the proximal end of the male fitting 220. The inner and outer diameters of the male sidewall 244 may be approximately equal to those of the female sidewall 144. The male stripout sealing layer 310 may be bonded to the proximal end surface 243 of the male connector through any suitable technique, for example, ultrasonic welding. The male stripout sealing layer 310 preferably seals the interior of the male connector 200 from the ambient environment. The male stripout sealing layer 310 preferably includes a pull tab that extends beyond the periphery of the connectors 100, 200 to allow removal when the connectors 100, 200 are joined.

When the female and male connectors 100, 200 are initially connected, the female and male stripout sealing layers 300, 310 preferably abut one another in face-to-face contact. For example, the diameters and locations of the female and male sidewalls 144, 244 and the lengths of the forks 146 and the sidewalls 144, 244 may be arranged to provide face-to-face contact of the stripout layers 300, 310 between the end surfaces 143, 243 of the sidewalls 144, 244 when the connectors 100, 200 are coupled. The dimensions may be arranged to provide not only contact but also a slight compression of the stripout layers 300, 310 between the end surfaces 143, 243. However, the compression is preferably not so large as to interfere with the removal of the stripout layers 300, 310 from between the sidewalls 144, 244. Of course, if the female and male connectors 100, 200 include non-removable sealing layers, rather than the stripout sealing layers 300, 310, then the compression may be somewhat larger. Alternatively, the dimensions and locations of the forks 146 and the sidewalls 144, 244 may be arranged to provide a slight space between the female and male stripout layers 300, 310. For example, the combined length of the sidewalls 144, 244 may be less than the distance between the flanges 142, 242. Preferably the space is sufficiently small to prevent significant axial movement of the connectors 100, 200 when they are connected to one another.

The stripout layers 300, 310 may comprise impermeable materials. such as glassine paper, metal foils, or impermeable polymeric films, or permeable materials. including papers such as Tyvek™ paper or porous polymeric films, which preclude the passage of bacterial contaminants. A preferred impermeable material is an aluminum foil which is removably sealed to the fitting 120,220. Permeable or porous materials offer the advantage, if desired, of allowing sterilizing gases, including ethylene oxide gas, to penetrate therethrough and spread to the interior of the female and male connectors 100, 200, thereby sterilizing them without having to remove the stripout layers 300, 310. Either permeable or impermeable materials may be suitable for gamma or heat sterilization. Additionally, a bacteriostatic or bacteriocidal compound or layer (not illustrated) may be disposed on either or both stripout layers 300, 310. The female stripout layer 300 may be the same as or different from the male stripout layer 310.

Although the illustrated embodiment depicts female and male connectors 100, 200 both with connecting ends sealed by removable sealing layers 300, 310, one or both of the connectors 100, 200 may additionally include a separate sealing layer, such as a pierceable membrane layer, which is not removable and is sealed to the connector under the stripout layer to provide an added level of sterility assurance. In other alternatives, the connectors 100, 200 may both include proximal ends sealed by sealing layers which are not removable, and the stripout layers may be omitted; or one connector may include only a stripout sealing layer while the other connector includes only a non-removable sealing layer.

Figure 8A:
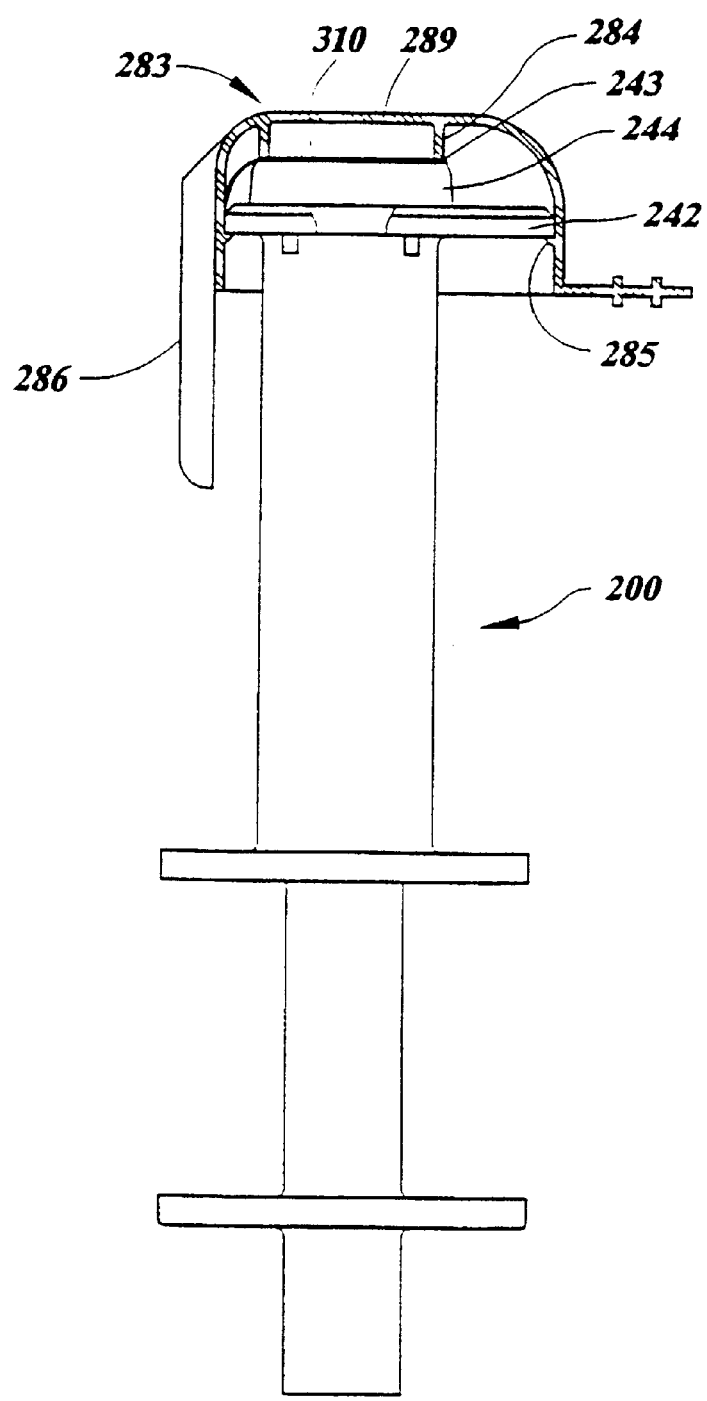
FIG. 8a is a side view in partial section of the male connector cap.
Figure 8B:
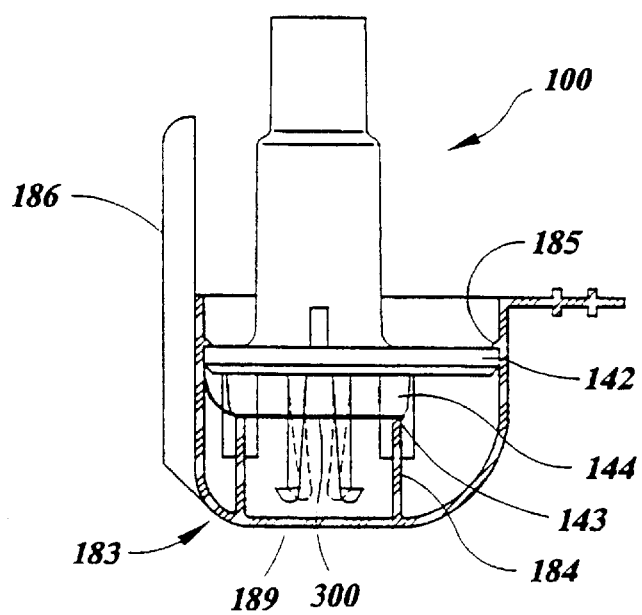
FIG. 8b is a side view in partial section of the female connector cap.
Figure 8C:
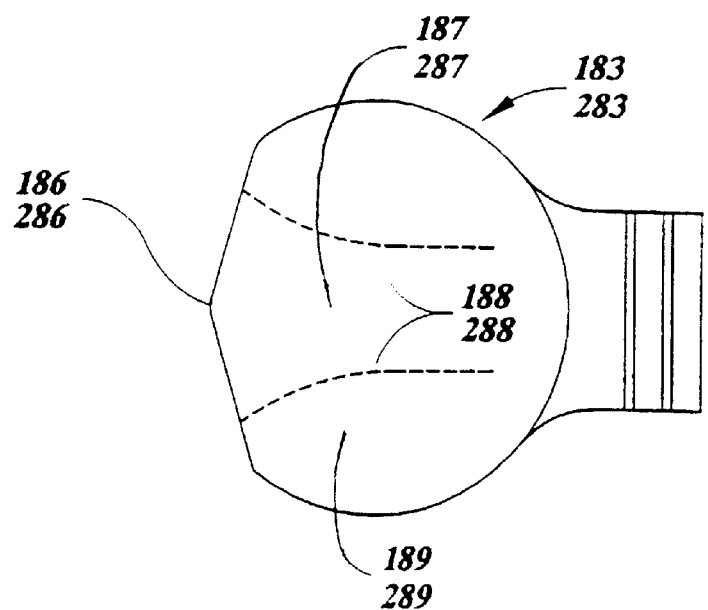
FIG. 8c is a top view of the male or female connector cap.

One, preferably both, of the connectors 100, 200 may also include a device which protects the proximal end of the connector 100, 200 and prevents the stripout layer 300, 310 from being inadvertently punctured or removed prior to assembly of the connectors 100, 200. Preferably the device is operatively associated with the proximal end of the connector 100, 200 and can be easily removed prior to the assembly of the connectors 100, 200. As shown in FIGS. 8a, 8b and 8c, an exemplary embodiment of the device may be a cap 183, 283 which may include a cover 189, 289, a tab 186, 286 attached to the cover, a cylindrical sleeve 184, 284, and a plurality of ribs 185, 285. Preferably the cover 189, 289 has a dome-shaped configuration, although the cover 189, 289 may have any other suitable configuration such as a cylindrical configuration. One of the ends of the sleeve 184, 284 is attached to the inner surface of the cover 189, 289. When the cap 183, 283 is mounted to the proximal end of the connector 100, 200, the other end of the sleeve 184, 284 bears against the end 143, 243 of the sidewall 144, 244, and the ribs 185, 285 engage the flange 142, 242 of the connector 100, 200. Thus, the sleeve 184, 284 and the ribs 185, 285 allow the cap 183, 283 to be securely mounted to the proximal end of the connector 100, 200. Further, the sleeve 184, 284 presses the stripout layer 300, 310 against the end 143, 243 of the sidewall 144, 244, holding the stripout layer 300, 310 in place and preventing it from being torn off. Preferably the height of the cover 189, 289 and the length of the sleeve 184, 284 are chosen such that the parts of the connector 100, 200 at the proximal end of the connector 100, 200, such as the stripout layers 300, 310 and the forks 146, can be contained in and protected by the cap 183, 283. Further, the tab 186, 286, which may be attached to the outer periphery of the cover 189, 289, preferably is sufficiently long such that the pulling tab 300, 310 are contained in and protected by the tab 186, 286. To make the cap 183, 283 easily removable, the cap 183, 283 may include a strip 187, 287 defined by perforations 188, 288 and connected to the tab 186, 286. Therefore, the cap 183, 283 can be easily removed from the connector 100, 200 by pulling the tab 186, 286 and tearing the strip 187, 287 along the perforations 188, 288. Once the strip 187, 287 is torn but may still be attached to the cap 183, 283, the cap 183, 283 can be easily removed from the connector 100, 200.

The cap 183, 283 may be formed from any suitable material which provides the cap 183, 283 with sufficient structural integrity and is sufficiently pliable such that the strip 187, 287 can be easily torn along the perforations 188, 288. Preferably the cap 183, 283 is formed from a plastic material or a metallic material, such as aluminum or aluminum alloy. More preferably the cap 183, 283 is formed from a polymeric material such as polycarbonate or polypropylene.

In accordance with one aspect of the present invention, the connector assembly includes at least one resilient sealing member, such as a male sealing member 270 disposed at the proximal end of male connector 200. For example, the male sealing member may be enclosed in a socket 245 formed on the proximal end of the male connector 200 and having an open end. In the illustrated embodiment, for example, in FIG. 2 and FIG. 3, the socket 245 is defined by the annular sidewall 244 at the connecting end of the male connector 200, and the open end comprises the proximal end surface 243 of the side wall 244. The socket 245 preferably completely surrounds the male sealing member 270; e.g., the side wall 244 preferably comprises a continuous, unbroken cylindrical wall which completely surrounds the male sealing member 270. The socket 245 and the male sealing layer 310 preferably sealingly contain the resilient sealing member.

Figure 2:
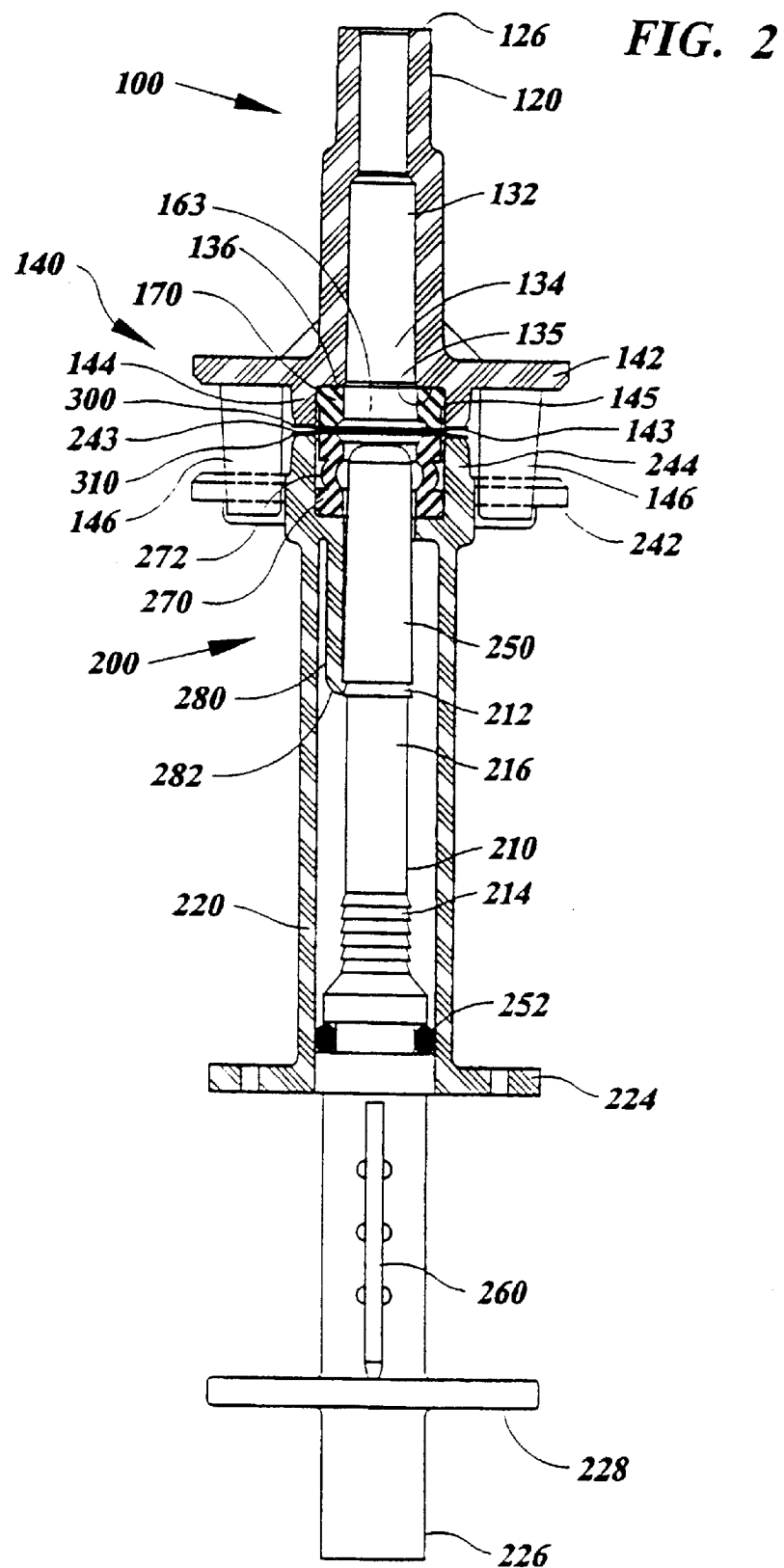
FIG. 2 is a side view in partial section of the connector assembly of FIG. 1.
Figure 6:
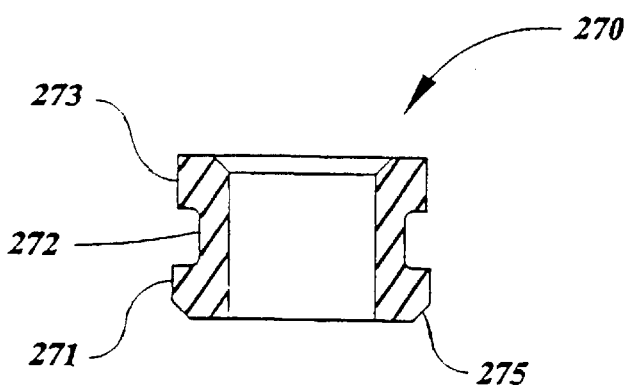
FIG. 6 is a sectional view of a male sealing member.

The male sealing member 270 can be variously configured. For example, the male sealing member 270 may comprise a resiliently compressible and expandable member including a hollow body having opposite open ends and an interior passage extending between the open ends, as illustrated in FIGS. 2, 3, and 6. The male sealing member 270 preferably comprises an annular base portion 271, neck portion 272, and head portion 273. The base portion 271 preferably comprises an annular rim having a slightly larger outer diameter than the inner diameter of the sidewall 244 and being adapted to form a tight frictional fit with the sidewall 244 when it is inserted in the socket 245 of the male connector 200. The base portion 271 may include a beveled surface 275 along its outer diameter to allow the base portion 271 to be inserted in and slide to the bottom of the socket 245.

The neck portion 272 of the male sealing member 270 preferably forms an annular wall joining the base portion 271 and the head portion 273. The wall of the neck portion 272, which is preferably thinner than the wall of the base portion 271 and thinner than the wall of the head portion 273, is preferably resiliently compressible to allow the male sealing member 270 to be compressed within the socket 245 of the male connector 200 by the male stripout layer 310. In the illustrated embodiment, the length of the male sealing member 270 is greater than the length of the male sidewall 244 and the thin wall neck portion 272 has an inner diameter equal to, and an outer diameter less than, those of the base portion 271 and the head portion 273. The neck portion 272 resiliently collapses, e.g., bends radially outwardly, to allow the sealing member 270 to be compressed within the socket 245 of the male connector 200. Alternative structures for the neck portion 272 are within the scope of the present invention. For example, the neck portion 272 may have a larger inner diameter than those of the base portion 271 and head portion 273 and may bend radially inward, or the neck portion 272 may comprise a bellows-like member having multiple bends when the male sealing member 270 is compressed.

The head portion 273 preferably comprises a beveled inner surface 277 and an annular rim which is formed on an end of the male sealing member 270 opposing the base member 271. Further, the head portion 273, as well as the neck portion 272, preferably has an outer diameter which is smaller than the outer diameter of the base portion 271 and is smaller than the inner diameter of the side wall 244 forming the socket 245. Because the outer diameters of the head portion 273 and the neck portion 272 are smaller than the inner diameter of the socket 245 and are spaced from the side wall 244 of the socket 245, they easily expand axially within the socket 245 without seizing or catching against the side wall 244. Thus, the head portion 273 and the neck portion 272 may resiliently expand from within the socket 245 to form a tight seal with the female connector 100 when the stripout layers 300, 310 are removed.

Figure 9:
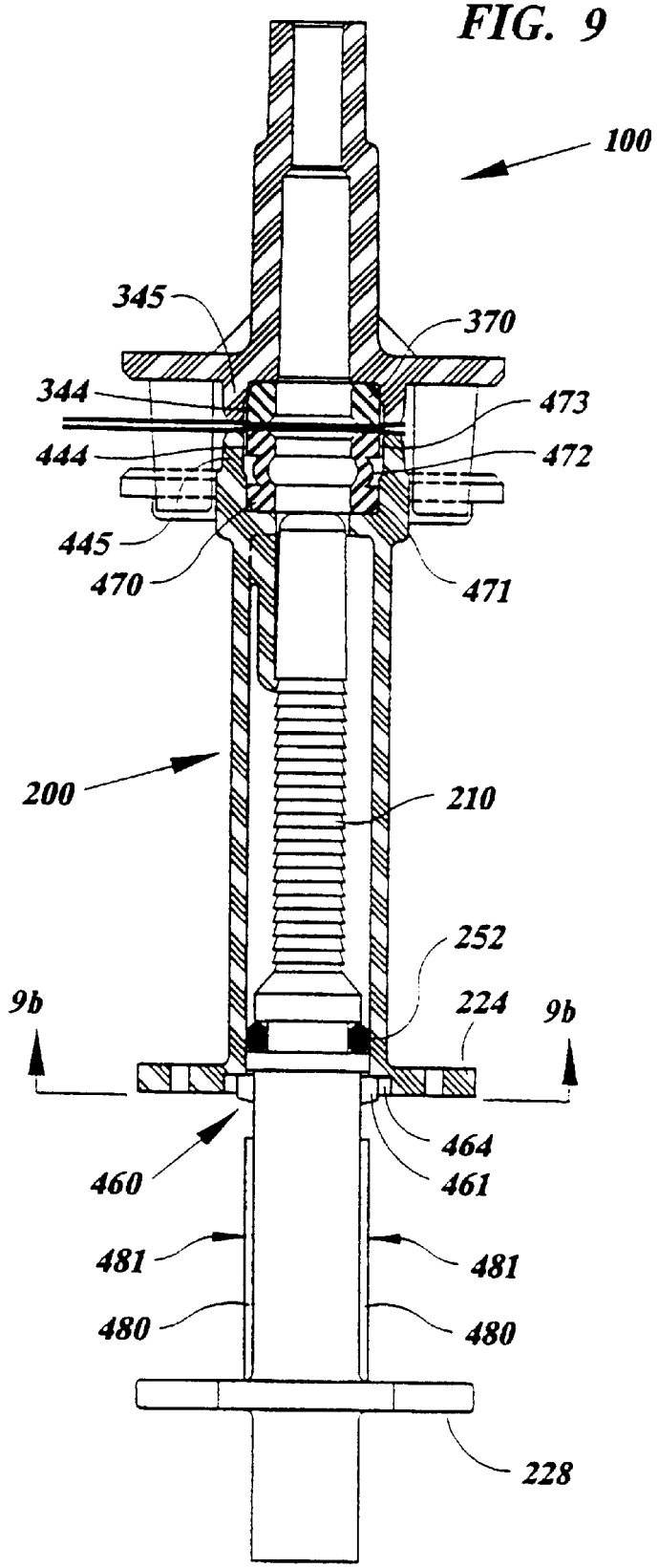
FIG. 9 is a side view in partial section of a connector assembly according to another embodiment of the present invention.

There are many alternative ways by which the male sealing member may be configured. Shown in FIG. 9, for example, is an alternative configuration. The male sealing member 470 shown in FIG. 9 is similar to the male sealing member 270 shown in FIG. 6 but has a head portion 473 and a base portion 471, which have substantially the same outer diameter. The socket 445, on the other hand, has a continuous cylindrical wall including an interior step in which the inner diameter of the distal portion of the socket wall 444 is smaller than that of the proximal portion of the socket wall 444. Preferably the inner diameter of the distal portion of the socket wall is slightly less than the outer diameter of the base portion 471 and is adapted to form a tight frictional fit with the base portion 471 when the male sealing member 470 is inserted in the socket 445. The inner diameter of the proximal portion of the socket wall 444 preferably is larger than the outer diameters of the head portion 471 and the neck portion 472 such that the head and the neck portions 471, 472 can easily expand axially within the socket 445 without seizing or catching against the proximal portion of the socket wall 444.

Although the illustrated embodiments depict the male sealing member 270, 470 as having a constant inner diameter and a varying outer diameter, a male sealing member with a constant outer diameter and variable inner diameter is within the scope of the invention. As long as the male sealing member is resiliently compressible and expandable, the male sealing member may have a varying inner diameter rather than a varying outer diameter. Alternatively, the male sealing member may have a varying inner diameter and a varying outer diameter or a constant inner diameter and a constant outer diameter.

A second sealing member, for example, a female sealing member 170, may be disposed in the socket 145 of the female connector 100. The socket 145, which also has an open end, includes the sidewall 144, which is preferably continuous and completely surrounds the female sealing member 170, and the proximal end surface 143 of the female fitting 120. The female sealing member is preferably sealingly contained within the socket 145 and the female stripout layer 300.

Figure 7:
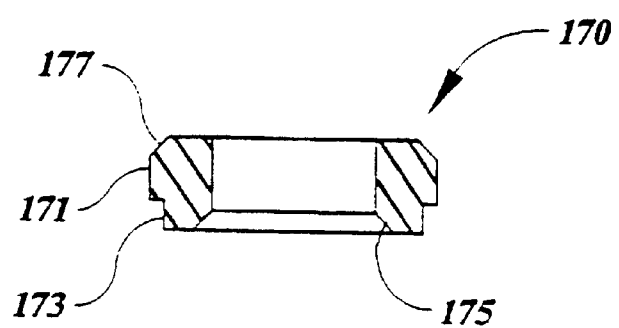
FIG. 7 is a sectional view of a female sealing member.

The female sealing member 170 may be variously configured. For example, the female sealing member 170 may also comprise a resiliently compressible and expandable member including a hollow body having opposite open ends and an interior passage extending between the open ends, as shown in FIGS. 2, 3, and 7. The female sealing member 170 preferably comprises a base portion 171 and a head portion 173. The base portion 171 preferably comprises an annular rim having an outer diameter larger than the inner diameter of the sidewall 144 and being adapted to form a tight frictional fit with the socket 145 of the female connector 100. The base portion 171 preferably also includes a beveled outer surface 175 to facilitate insertion of the female sealing member 170 into the bottom of the socket 145.

The head portion 173, as well as the base portion 171, preferably comprises a resiliently compressible material to allow the female sealing member 170 to be compressed within the socket 145 of the female connector 100. The head portion 173 preferably has an outer diameter which is smaller than the outer diameter of the base portion 171 and is smaller than the inner diameter of the side wall 144 forming the socket 145. Because the outer diameter of the head portion 173 is smaller than the inner diameter of the socket 145 and is spaced from the side wall 144 of the socket 145, the head portion 173 easily moves axially within the socket 145 without seizing or catching against the side wall 144. Thus, the head portion 173 may resiliently expand within the socket 145 to form a tight seal with the male connector 200 when the stripout layers 300, 310 are removed. The head portion 173 preferably comprises an inner diameter and a beveled inner surface 177 which mirror the inner diameter and the beveled inner surface 277 of the male sealing member 270 to form an annular indention 163 in an inner surface of the joined sealing members 170, 270 when the stripout layers are removed. Further, the head portion 173 may have a thinner wall than that of the base portion 171.

There are also many alternative ways by which the female sealing member may be configured. Shown in FIG. 9, for example, is an alternative configuration. The female sealing member 370 shown in FIG. 9 is similar to the female sealing member 170 shown in FIG. 7 but has a uniform outer diameter. The socket 345, on the other hand, has a continuous cylindrical wall including an interior step in which the inner diameter of the distal portion of the socket wall 344 is smaller than that of the proximal portion of the socket wall 344. Preferably the inner diameter of the distal portion of the socket wall 344 is slightly less than the outer diameter of the female sealing member 370 and is adapted to form a tight frictional fit with the female sealing member 370 when the female sealing member 370 is inserted in the socket 345. The inner diameter of the proximal portion of the socket wall 344 preferably is larger than the outer diameter of the female sealing member 370 such that the female sealing member 370 can easily expand axially within the socket 345 without seizing or catching against the proximal portion of the socket wall 344.

The sealing member or members provide several advantages. For example, each sealing member 170, 270 may be formed from a different material than the material forming the fittings 120, 220. In particular, each sealing member may be formed from a material which is more resilient, e.g., more resiliently compressible and expandable, than the more rigid material forming the fittings 120, 220. Exemplary materials for the sealing members include resiliently compressible and expandable polymeric materials or elastomeric materials. A preferred material is a TPE (thermoplastic elastomer), such as a Santoprene TPE. The enhanced resiliency of the sealing member(s) provides a greatly improved seal. Another advantage of the sealing member or members is that the end surface of the head portion 173, 273 may be formed very evenly, providing an excellent seal. In preferred embodiments, the end surfaces of the head portions 173, 273 of the contained sealing members 170, 270 abut but are not joined to the stripout layers 300, 310, i.e., the stripout layers are joined only to the end surfaces 143, 243 of the cylindrical walls 144, 244. This allows the end surfaces of the head portions 173, 273 to remain even and clean and, thereby, form a tight seal free of any leachants. Of course, in less demanding applications, the stripout layers may be joined to both the sidewalls and the sealing members or only to the sealing members.

Although the illustrated embodiment depicts the female sealing member 170 being sealed in the socket 145 of the female connector 100 by the female stripout layer 300, and the male sealing member being compressed and sealed within the socket 245 of the male connector 200 by the male stripout layer 310, alternative arrangements are within the scope of the present invention. For example, the male sealing member 270 may be disposed in the socket 145 of the female connector 100, and the female sealing member 170 may be disposed in the socket 245 of the male connector 200. Alternatively, the female sealing member 170 may be omitted. In an embodiment in which the female sealing member 170 is omitted, the male sealing member 270 may be disposed within the socket of either connector by a stripout layer or a non-removable sealing layer.

In an embodiment which includes a single sealing member, when the stripout layer is removed, the sealing member may abut a surface on the connecting end of the opposing connector to seal the connector assembly. For example, if the male sealing member 270 is disposed in the socket 245 of the male connector 200, the head portion 273 of the connector may contact a surface 135 in the counterbore 136 of the female connector 100. Alternatively, the sidewall 144 of the female connector may be thickened in a radially inward direction to extend inwardly beyond the sidewall 244 of the male connector and provide a contact surface for the male sealing member 270. The male connector 200 preferably includes a stem 210 telescopically housed in a generally cylindrical body 221 defining the aperture 232 in the male fitting 220. The male connector 200 is also preferably adapted to contain and conduct fluid communication and preferably defines an isolated portion of the fluid flow path, e.g., containing or conducting isolated fluid communication. Accordingly, the stem 210 is preferably sealed within the aperture 232 defined by the fitting 220. In the illustrated embodiment, the stem 210 includes a seal 252 coupled between a distal end 226 of the stem 210 and the body 221 of the male connector 200. The seal 252 may comprise an oaring disposed around the stem 210. In an alternative embodiment, the seal 252 may be disposed in a groove in the interior wall of the body of the male connector 200. The seal 252 preferably sealingly and slidably engages an interior wall to seal the aperture 232 from the ambient environment and allow the stem 210 to move axially.

While the stem 210 may be arranged to move axially only with respect to the female connector 100 and to be stationary with respect to the male fitting 220, the stem 210 is preferably arranged to move axially both with respect to the female connector 100 and the male fitting 220. For example, the stem 210 preferably moves axially through the male fitting 220; e.g., through the aperture 232 and the open proximal end of the aperture 232, through the socket 245 and the open end of the socket 245, through the male sealing member 270 including the, open ends and the interior passage, and/or through any non-removable sealing layer. Further, the stem 210 preferably moves axially into the female connector 100; e.g., through any non-removable sealing layer, through the female sealing member 170 including the open ends and the interior passage, through the open end of the socket 145 and the socket 145, through the open end of the aperture 132, and/or into the aperture 132. Because the stem 210 moves through the female and/or male sealing members, the largest outer diameter of the stem 210 is preferably smaller than the smallest inner diameter of the interior passages of the sealing members 170, 270. Further, the proximal portion of the stem 210 preferably is tapered and has a bullet-shaped configuration, as shown in FIG. 9.

This facilitates axial movement of the stem 210 without disturbing the seal formed by the sealing members 170, 270. Alternatively, the diameters may be approximately equal to create a seal between the stem 210 and the sealing member or members 170, 270.

The stem 210 is preferably hollow, defining a lumen (not shown) therein. The proximal end of the stem 210 may have a head 250 formed thereon. The head 250 may have an aperture providing fluid access between the lumen and the exterior of the stem 210. The head 250 may comprise a blunt member or a piercing member, depending on whether or not the sealing layers include non-removable layers. For example, if the sealing layers include non-removable layers in addition to stripout layers, the head 250 preferably comprises a piercing member to pierce the non-removable layers and provide fluid communication between the interior regions of the male and female connectors 200, 100. If separate non-removable layers are not included, the head 250 may comprise a blunt member. The head 250 may be blunt because once the stripout members are removed, there are no obstructions which require piercing between the male and female connectors 200, 100.

Figure 11:
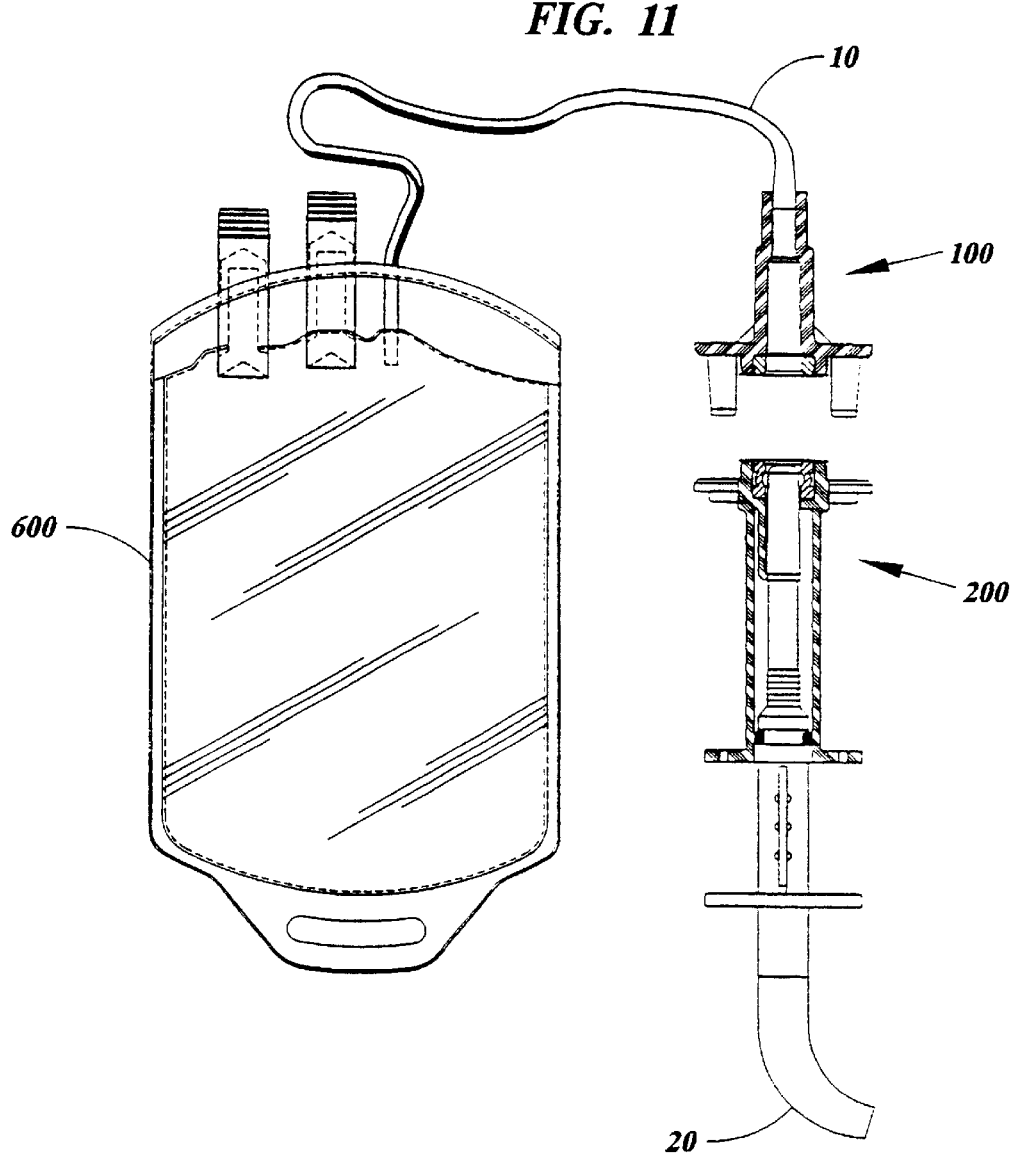
FIG. 11 is an elevation view, in partial section, of disassembled components of a fluid system according to another embodiment of the present invention.
Figure 12:
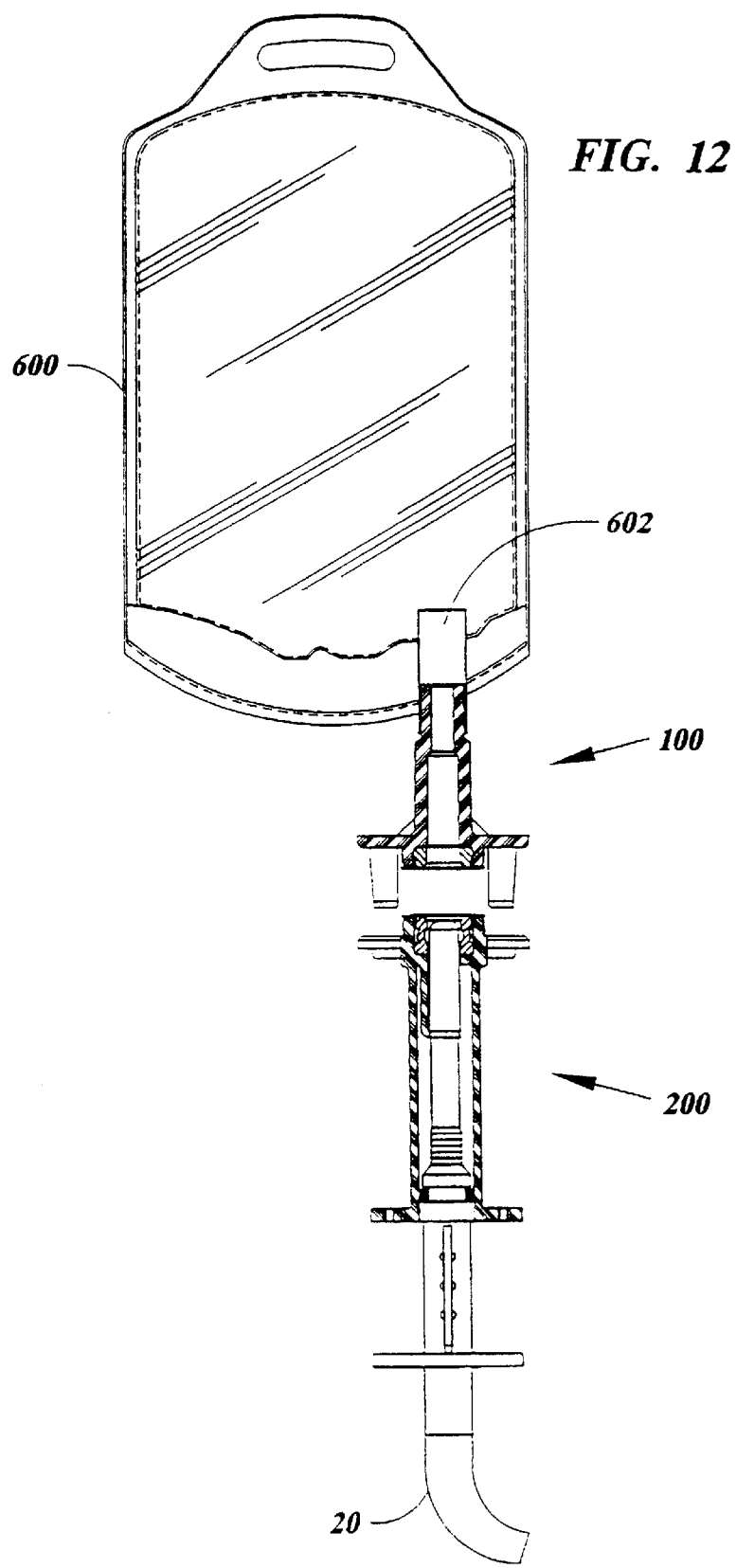
FIG. 12 is an elevation view, in partial section, of disassembled components of a fluid system according to another embodiment of the present invention.
Figure 14:
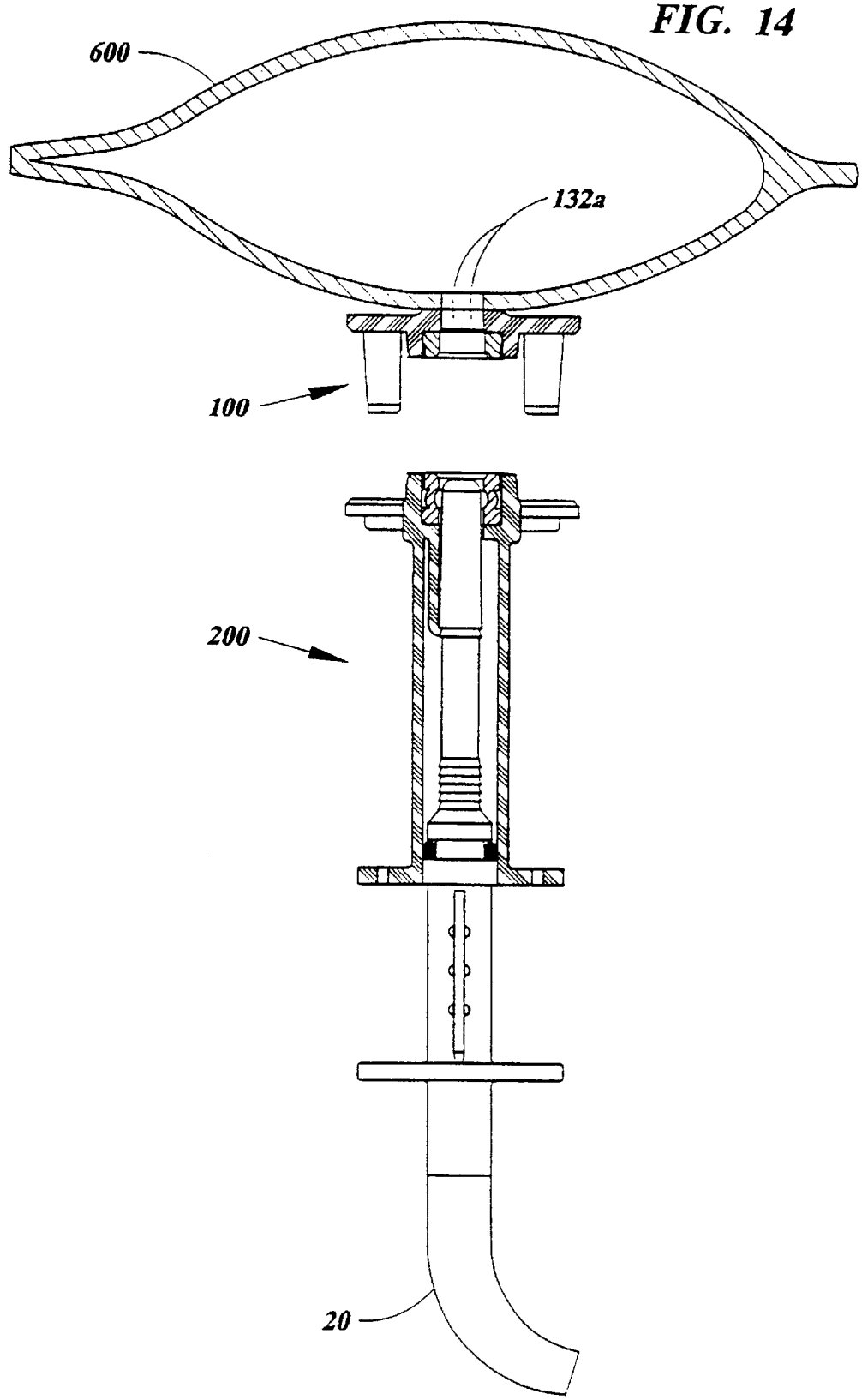
FIG. 14 is an elevation view, in partial section, of disassembled components of the fluid system of FIG. 11

The stem 210 may also be connected to a fluid container or conduit 20 as best shown on FIGS. 11, 12, and 14. For example, a conduit 20, such as a section of tubing, may be connected to the distal end 226 of the stem 210 in any suitable manner, e.g., by using solvents, bonding agents, hose clamps, ultrasonic welding, threaded connectors, or friction fitting. Alternatively, the tubing 20 or container may be molded integrally with the stem 210.

According to another aspect of the present invention, the stem 210 may include a locking device. The locking device 260 may be of any configuration that restricts the accidental or inadvertent axial advancement of the stem 210. In the embodiment illustrated in FIG. 1, the locking device comprises two locking tabs 260 rigidly extending axially from a lower flange 224 of the body 221 to a flange 228 on the stem 210. The number of locking tabs 260 is not critical to the invention. For example, a single locking tab 260 may be included, or more than two locking tabs 260 may be included. If multiple locking tabs 260 are included, they are preferably located at equally spaced circumferential locations about the stem 210 to uniformly distribute force applied to the stem 210.

In the embodiment shown in FIG. 1, the locking tabs 260 comprise radially projecting fins which extend axially between the flanges 224, 228. The locking tabs 260 may be deformable, e.g., may be arranged to bend out of the way or to break away from one or both of the flanges 224, 228. For example, the locking tabs 260 may be attached at bendable or frangible joints 262 to the flange 228 and/or the barrel of the stem 210. The locking tabs 260 are preferably not attached to the distal flange 224 of the male fitting 220. Thus, each locking tab 260 may be easily grasped and bent in a direction perpendicular to the plane of the tab 260, breaking the frangible joint and freeing the stem 210 to move axially. In an alternative embodiment, the locking device may comprise a permanently attached, non-breakable arrangement, such as a radially extending key on the stem 210 and a keyway on the body 221 which allows the axial movement of the key, and stem 210 after the key is aligned with the keyway. Alternatively, the stem 210 may include one or more keyways and the body 221 may include one or more keys.

Figure 10:
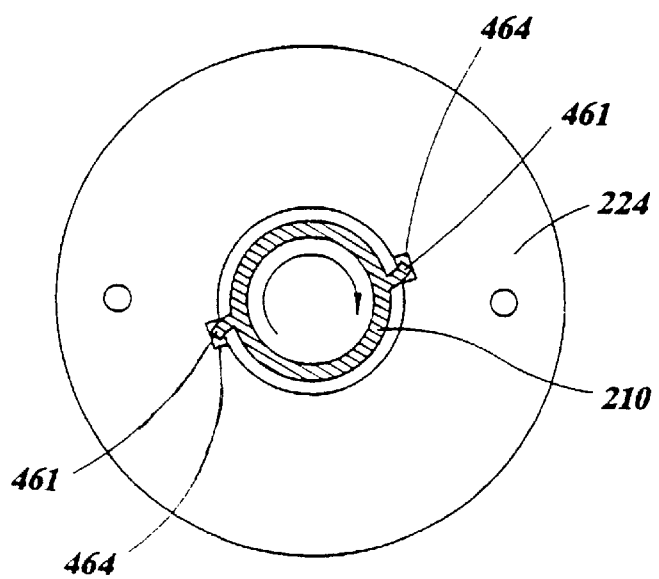
FIG. 10 is a bottom view in partial section of the male connector of FIG. 9.

Shown in FIGS. 9 and 10 is a preferred embodiment of the locking device 460. The locking device 460 may comprise one or more wings 461 extending radially from the surface of the stem 210, although the locking device 460 shown in FIGS. 9 and 10 comprises two wings 461. The wings 461 extend radially beyond the inner diameter of the male fitting 220 and may abut the distal surface of the flange 224, thus preventing the stem 210 from being inadvertently advanced within the male fitting 220. In order to advance the stem 210, the stem 210 may be rotated. The rotation of the stem 210 pushes the wings 461 tangentially against a structure that can apply a tangential force to the wings 461. As a result, the wings 461 bend tangentially and fold away from the distal surface of the flange 224, thus allowing the stem 210 to advance within the male fitting 220. For example, in FIGS. 9 and 10, each of the wings 461 is disposed within a slot 464 on the distal surface of the flange 224. When the stem 210 is rotated, the rotation of the stem 210 pushes the wings 461 against the sidewalls of the slots 446 and bends the wings 461 tangentially, thus allowing the stem 210 to advance within the male fitting 220. Alternatively, the distal surface of the flange may include protrusions instead of slots, and the rotation of the stem pushes the wings against the protrusions and bends the wings tangentially, thus allowing the stem to advance within the male fitting. The locking device shown in FIGS. 9 and 10 is preferred because nothing needs to be broken off and therefore, there are no loose pieces associated with the locking device.

A purpose of the locking devices is to restrict the accidental or inadvertent axial advancement of the stem 210. Preferably, an operator does not unlock the locking device until the male connector 200 and the female connector 100 are joined and the stripout layers 300, 310 are removed. If the locking device is unlocked before the connectors 100, 200 are joined and the stripout layers 300, 310 are removed, the stem 210 may damage the stripout layer 300 and compromise the sterility of the male connector 200.

In addition to the locking device, the male connector 200 may also comprise a ratchet structure. For example, as shown in FIGS. 2 and 3, the stem 210 may comprise first and second sets of beveled annular ribs 212, 214 circumfusing the external surface of the stem 210. The ribs 212, 214 may be beveled such that they project from the surface of the stem 210, extending distally toward the flange 228 of the stem 210 and forming an acute angle with the external surface of the stem 210. The first set of ribs 212 is preferably spaced from the second set of ribs 214 by a smooth surface 216 formed on the stem 210. A catching member 280 is preferably coupled to the inner wall of the body 221 of the male connector 200. A distal end of the catching member 280 includes a catch 282 which rests on the outer surface of the stem 210. A similar ratchet structure is shown in FIG. 9 and disclosed in Matkovich U.S. Pat. No. 5,393,101, which is incorporated by reference to support this and other features of the present invention. The ratchet structure shown in FIG. 9 comprises a single set of annular ribs and preferably does not include a smooth surface section. The ratchet structure in U.S. Pat. 5,393,101 is preferred because the stem is not retractable once the head is advanced toward the female fitting and can only move toward the female fitting.

The stem 210 may further include a device disposed between the male fitting 220 and the stem 210, which stabilizes the stem 210 when the stem 210 is advanced within the male fitting 220. An exemplary embodiment of the device, as shown in FIG. 9, may include a plurality of axially extending ribs 480. The ribs 480 may be mounted, for example, on the stem 210 between the O-ring 252 and the flange 228 and preferably are equally spaced circumferentially around the stem 210. The outer surfaces 481 of the ribs 480 may define a cylinder that has a diameter similar to the inner diameter of the male fitting 220. Thus, when the stem 210 is advanced within the male fitting 220, the outer surfaces 491 of the ribs 490 contact the inner surface of the male fitting 220, which stabilizes the stem 210 as it moves along within the male fitting 220.

In operation, to join the connectors, an operator first removes the caps 183, 283 protecting the proximal ends of the connectors 100, 200 by pulling the tabs 186, 286 and tearing the strips 187, 287 along the perforations 188, 288. The operator then interlocks the connectors. In the illustrated embodiments, interlocking the connectors comprises sliding the forks 146 in the female connector 100 into the slots 240 in the male connector 200 until the catches 148 abut against the distal surface of the flange 242. As shown in FIG. 1, the forks 146 may bend slightly as the catches 148 at the ends of the forks 146 move through the slots 240.

The interlocking mechanism may be configured to ensure that the tabs of the stripout layers 300, 310 both extend in the same direction when the connectors 100, 200 are interconnected. For example, the forks 146 and slots 240 may be arranged in sets such that the forks 146 only engage the slots 240 when the tabs extend in the same direction. In the illustrated embodiment, one set of forks and slots are closely spaced while the other set of forks and slots are more distantly spaced. The tabs, forks, and slots are all arranged such that the connectors 200 will interconnect only when the closely spaced forks engage the closely spaced slots, the distantly spaced forks engage the distantly spaced slots, and the tabs extend in the same direction from the stem.

Once the connectors 100, 200 are coupled, the stripout layers 300, 310 are removed, which in the illustrated embodiment places the apertures 132, 232 of the connectors 100, 200 in fluid communication with each other. Any contaminants entrained on the external surfaces of the stripout layers 300, 310 may be removed with the stripout layers 300, 310.

As each stripout layer 300, 310 is removed, one or both of the male and female sealing members 270, 170, which were compressed in the male and female sockets 245, 145, expand to contact each other and seal the connectors 100, 200. The sealing members preferably maintain the seal throughout the process of removing the stripout layers 300, 310. More particularly, as the stripout layers are withdrawn the exposed portions of the sealing members 170, 270 expand and contact one another, creating a seal between the contacting exposed portions. Because contact between the sealing members follows the withdrawing stripout layers, the seal is immediately created behind the stripout layers 300, 210 as the stripout layers are withdrawn.

To contact the female sealing member 170, the resiliently compressible head portion 273 and/or neck portion 272 of the male sealing member 270 axially expands from a compressed state to an expanded state where the distance between the base 271 and head 273 portions is increased. The head portion 173 of the female sealing member 170 may also expand. The head portion 273 of the male sealing member 270 abuts against the head portion 173 of the female sealing member 170 to form the seal. Because the male sealing member 270 and the female sealing member 170 each comprise a resiliently compressible and expandable member, movement of the male connector 200 or the female connector 100 once they are coupled does not reduce the seal. The male and female sealing members 270, 170 expand or compress to counteract any movement of the connectors 100, 200 and tightly maintain the seal. The annular groove 163 may decrease the surface area of the contact between the sealing members and thus increase the axial pressure exerted on one sealing member by the other, thereby strengthening the seal. Thus, a tight, sterile connection is created and maintained.

Once the stripout layers 300, 310 are removed, the head 250 of the stem 210 is preferably extended into the female connector 100. In order to move the head axially, an operator unlocks the locking device, for example, by grasping and breaking the locking tabs 260 away from the flange 228 of the stem 210 in the case of the embodiment shown in FIG. 1, or by rotating the stem 210 to deform the wings 480 tangentially in the case of the embodiment shown in FIGS. 9 and 10. The operator then slides the flange 228 of the stem 210 axially towards the lower flange 224 of the male connector 200. As the stem moves axially, the stem 210, including the head 250, moves through the male fitting 220 and the female connector 100 as previously described. Further, the seal 252 slides along the inner wall of the male connector 200; the catching member 280 slides along the first ribbed surface 212 and the smooth surface 216 and then latches along the second ribbed surface 214; and the head 250 then lodges in the bore 134 of the female connector 100. The bore 134 is preferably tapered so the head 250 lodges in frictional sealing engagement with the wall of the bore 134. Fluid may then flow freely without contamination through the aperture 132 in the female connector 100 and the lumen in the stem 250 via the sterile connection of the female and male connectors 100, 200.

The connector assembly may be utilized in conjunction with various fluid systems or devices, such as those including flexible and/or rigid fluid containers, a syringe, a drip chamber, a filtration device, an intravenous (IV) device, or any combination thereof. For example, the connector assembly may be combined with intravenous (IV) devices and used to supply fluids, for example, parenteral and biological fluids. As used herein, a parenteral fluid is a physiologically acceptable fluid, which is preferably sterile. Examples of parenteral fluids include saline solution, i.e., isotonic (about 0.9%) sterile saline solution, and an electrolyte solution, including for example, dextrose 5% in water (D5W). Biological fluids, as used herein, are fluids originating from a living organism, for example, blood and blood components. Examples of biological fluids for which the present invention may be suitable include whole blood, packed red cells, platelet rich plasma, platelets and plasma.

An exemplary embodiment of a fluid system including a connector assembly is illustrated in FIG. 11, where analogous components have the same reference numbers as the connector assembly of FIGS. 1–7. In FIG. 11, the female connector 100 of a connector assembly is connected to a container 600 via a conduit 10. The conduit 10, as described previously, may be connected to the female connector 100, for example, at the distal end 126, in any suitable manner, e.g., by utilizing solvents, bonding agents, hose clamps, ultrasonic welding, threaded connectors, or friction fitting. Alternatively, the conduit 10 may be molded to the female connector 100 as an integral part thereof.

The conduit 10 may be connected to the container 600 through a fitment (not shown in FIG. 11) which allows fluid communication between the conduit 10 and the container 600. The fitment (not shown in FIG. 11) may include a valve such as a transfer leg closure which controls fluid flow to or from the container 600. The female connector 100, the conduit 10, and the container 600 may be constructed as a single, integral unit.

The conduit 20 connected to the male connector 200 of the connector assembly may be connected to other components comprising the fluid system (not illustrated). For example, the conduit 20 may be connected to a syringe, to a drip chamber, to a patient or to a filtration device. In addition, although not illustrated, the male connector 200 of the connector assembly may be connected to the container 600, i.e., the positions of the male and female connectors 200, 100 may be reversed. In such an embodiment, the male connector 200, the conduit 20, and the container 600 may be constructed as a single, integral unit.

The container 600 as well as the conduits 10, 20, which may be utilized in accordance with the connector assembly of the present invention, may be constructed of any material compatible with parenteral and biological fluids. The composition of the container 600 and the conduits 10, 20 may vary with the nature of the particular fluid utilized. A wide variety of suitable containers 600 and conduits 10, 20 are already known in the art. Exemplary containers 600 include but are not limited to syringes, flexible bags, and rigid containers. The container 600 may be formed from various materials such as metallic materials, glass, and plastics, including polyvinyl chloride (PVC). The container 600 preferably comprises plasticized PVC for flexibility and strength. Typical conduits 10, 20 include tubing comprising flexible plastics, such as plasticized PVC, for ease of use. It is intended that the invention should not be limited by the type or composition of the container 600 and/or conduits 10, 20 being employed.

The fluid system illustrated in FIG. 12 is similar to the fluid system illustrated in FIG. 11 and analogous components have the same reference numbers. In this embodiment, however, the female connector 100 may be connected directly to the container 600. For example, the female connector 100 may be fitted with a fitment such as a transfer leg closure. In contrast to the female connector 100 illustrated in FIG. 11, wherein the conduit 10 is connected to the female connector 100, the connector 100 may be mounted directly to the fitment 602 of the container 600. The female connector 100 and the container 600 may be constructed as a single, integral unit.

As described above, the fluid conduit 20 connected to the male connector 200 of the connector assembly may be connected to other components in the fluid system. For example, the conduit 20 may be connected to a syringe, to a drip chamber, to a patient, or to a filtration device. In addition, although not illustrated, the male connector 200 of the connector assembly may be connected directly to the container 600.

In operation, the male and female connectors 200, 100 of the fluid systems of FIGS. 11 and 12 may be interlocked as previously described. Once interlocked, the stripout layers 300, 310 are removed, the stem 210 is moved through the male fitting 200 and sealing member 270, through the female sealing member 170 and into the aperture 132 of the female fitting 120, thereby forming a sterile fluid path through the fluid system.

Figure 13:
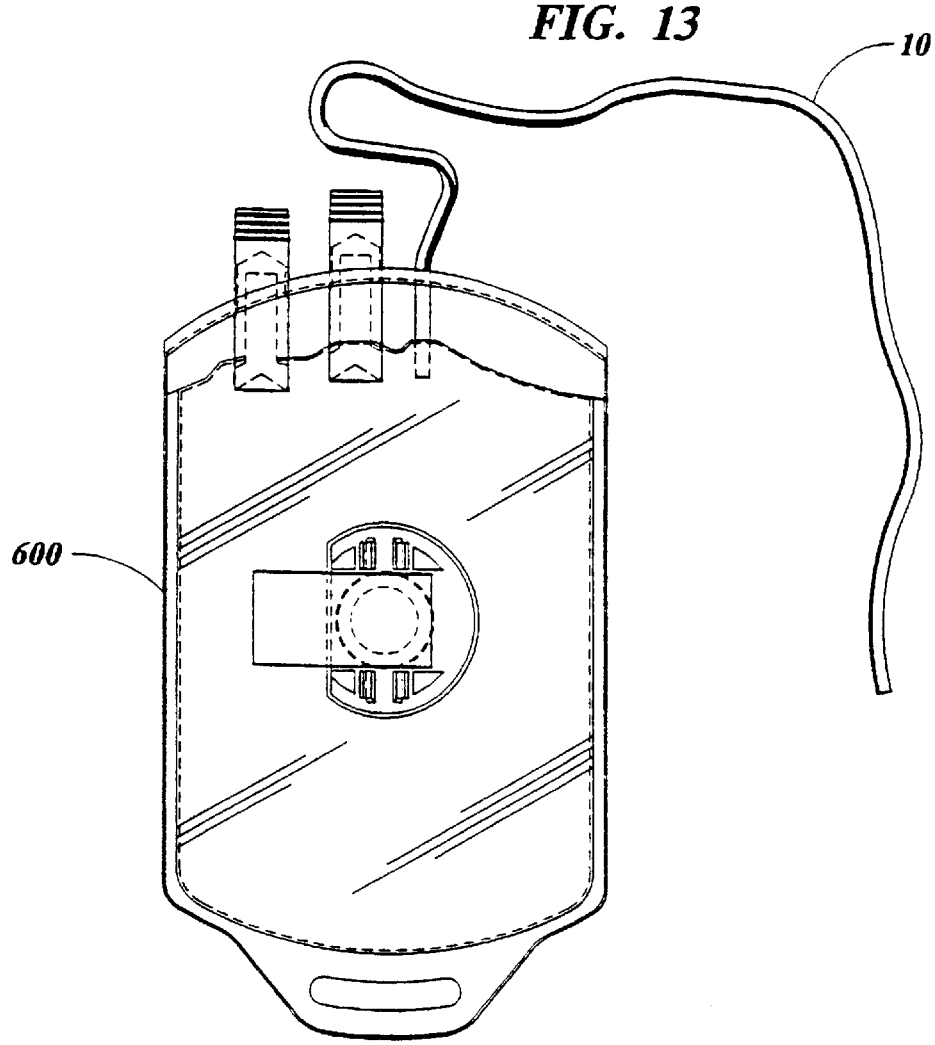
FIG. 13 is an elevation view of a fluid system according to another embodiment of the present invention.

FIGS. 13 and 14 illustrate an exemplary embodiment of a fluid system wherein a modified female connector 100 of the connector assembly is mounted directly to the wall of a container 600. Once again, analogous components have the same reference numerals as used in FIGS. 1–7 and 11–12. In this embodiment, the female connector 100 is different from the previously described female connectors 100. Essentially, in this embodiment, the female fitting 120 includes only the bracket 140. As in the previously described embodiments, the bracket 140 may be variously configured. The bracket 140 may comprise a socket 145 or cup having any suitable plan form, for example, the representative bracket 140 in the illustrated embodiment comprises a generally C-shaped member. A female sealing member 170 may be disposed within the socket 145 of the bracket 140 to aid the sterile connection of the connection assembly as previously described. In addition, the proximal end of the female connector 100 may have a Sealing layer, such as the previously described female stripout layer 300, to further aid the sterile connection of the connector assembly. The bracket 140 may also include a flange 142 with forks 146, as previously described, in order to aid the interlocking of the female connector 100 with the male connector 200. Alternative arrangements for the connection of the female and male connectors 100, 200 are also possible, and may include, for example, threaded connectors. In an alternative embodiment, the fitting 120 of the female connector 100 may extend beyond the container wall into the interior of the container 600.

The female connector 100 may be connected to the wall of the container 600 by a variety of means. In the exemplary embodiment illustrated in FIG. 13, the female connector 100 is connected to a major surface of the container 600. The female connector 100 may be bonded or welded to the container 600 or may be formed integrally therewith. The area of the wall where the female connector 100 is connected may be reinforced so that the female connector 100 will not tear away a portion of the wall. The reinforcement may be in the form of a grommet or any other suitable reinforcement means.

In operation, the male and female connectors 200, 100 of the fluid system of FIGS. 13 and 14 may be interlocked as previously described. Once interlocked, the stripout layers 300, 310 are removed, and the stem 210 is moved through the male fitting 220 and sealing member 270, through the female sealing member 170 and an aperture 132a in the female fitting 120, and through the wall of the container 600, thereby forming a sterile fluid path therethrough. To facilitate piercing of the container wall, the head 250 of the stem 210 may include a piercing member. The aperture 132a may be sized to seal against the head 250 of the stem 210, which is preferably tapered to provide an increasingly snug fit and seal at the walls of the bracket 140 defining the aperture 132a. Alternatively, the female connector 100 may comprise an O-ring to provide a fluid tight seal between the head 250 and the aperture 132a.

The connector assembly of any of the previous embodiments can be used to make either a wet connection or a dry connection, although preferably it is used to make a dry connection. A wet connection is one in which the male and female connectors 100, 200 are joined while there is liquid in one or both of the connectors 100, 200. A dry connection is one in which the connectors 100, 200 are joined without liquid in the connectors 100, 200, and the fluid flow through the connectors 100, 200 is established after the connectors 100, 200 are joined.

There are various ways to make a dry connection. For example, a fluid blocking mechanism may be used to block fluid flow from a fluid source to a connector 100, 200 before the connectors 100, 200 are joined and to open fluid flow after the connectors 100, 200 are joined. The fluid blocking mechanism may be any device which can block and open fluid flow to a connector 100, 200. The fluid blocking mechanism may be operatively associated with the connector 100, 200, disposed between the connector 100, 200 and the fluid source, or operatively associated with the fluid source. If only one connector 100, 200 is connected to a fluid source, only one fluid blocking mechanism may be used. On the other hand, if both connectors 100, 200 are connected to a fluid source, two fluid blocking mechanisms may be used.

Figure 15:
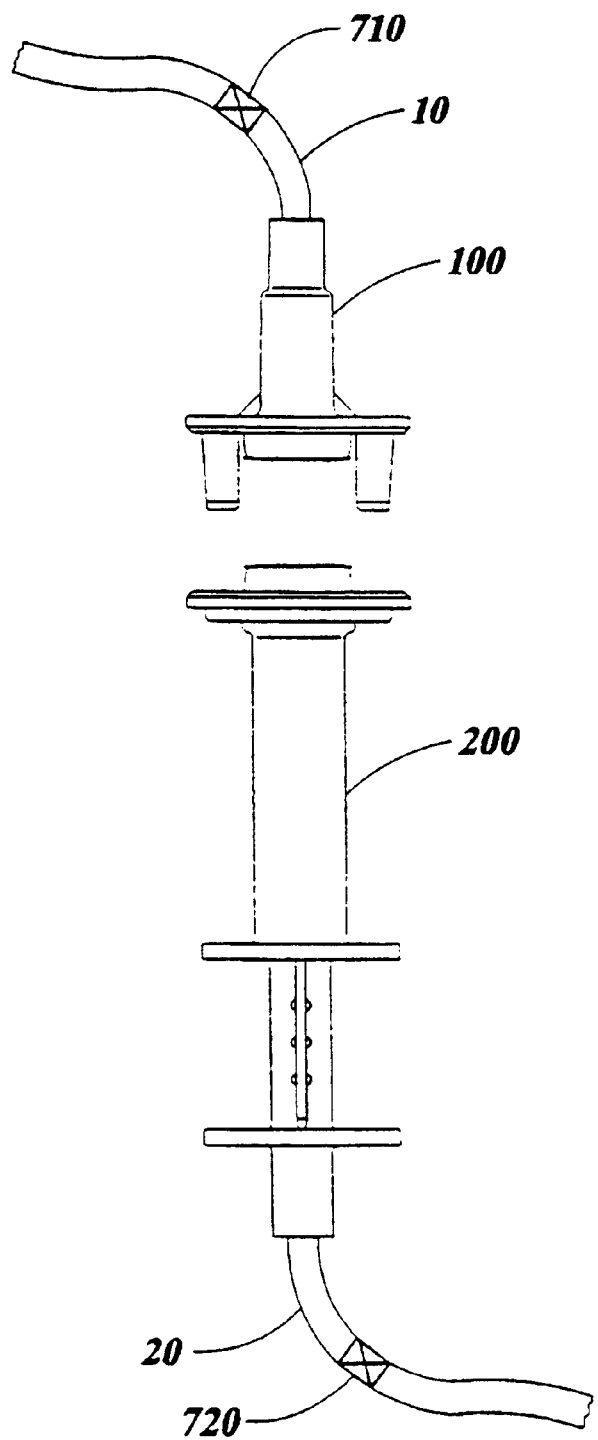
FIG. 15 is a diagram of the connector assembly of FIG. 1, which is used to make a dry connection.

Shown in FIG. 15 is a preferred arrangement for a dry connection. In the arrangement, a flow blocking mechanism 710, 720 is associated with the tubing 10, 20 attached to each of the male and the female connectors 100, 200. The flow blocking mechanism 710, 720 is preferably placed a short distance from the male and the female connectors 100, 200, e.g., within about 5 inches or more. The flow blocking mechanism 710, 720 can be any device which can selectively open and block the fluid flow to the connectors 100, 200, such as a valve or a clamp mounted to the exterior of the tubing 10, 20 and pinching the tubing 10, 20 closed. More preferably, the flow blocking mechanism 710, 720 is a breakaway type mechanism disposed in the interior of the tubing 10, 20. The breakaway type mechanism normally blocks fluid flow. However, when it is pinched, bent or otherwise manipulated by an operator, a portion of the mechanism moves, e.g., breaks away, and allows fluid flow through the mechanism. A breakaway type mechanism is disclosed in U.S. Pat. No. 4,586,928, which is incorporated by reference to support this and other features of the present invention.

In a preferred method of joining the male and female connectors 100, 200, the flow blocking mechanism 710, 720 is arranged such that no liquid flows past the mechanism 710, 720 to the connector 100, 200. Consequently, neither the male nor the female connector 100, 200 has any liquid in it as they are joined. The connectors 100, 200 are joined as previously described such that they are locked together with the head 250 of the stem 210 securely inserted within the aperture 132 of the female fitting 100. The flow blocking mechanism 710, 720 is then opened to allow fluid flow through the connector assembly.

Although shown and described is what are believed to be the most practical and preferred embodiments, it is apparent that departures from specific methods and designs described and shown will suggest themselves to those skilled in the art and may be used without departing from the spirit and scope of the invention. One of many examples of these alternative embodiments is a connector assembly in which a non-removable, pierceable membrane layer extends across the interior of one or both of the sealing members. The stem may then include a piercing member which would pierce the membrane layer(s) as the stem moves axially into the female fitting. Consequently, the present invention is not restricted to the particular features described and illustrated, but should be construed to cohere with all modifications and alternatives that may fall within the scope of the appended claims.

What is claimed is:

1. A connector assembly comprising:

a first fitting including an aperture;

a second fitting coupleable to the first fitting and having an aperture;

a socket cooperatively arranged with one of the first and second fittings and including a side wall;

a resilient sealing member disposed in the socket, wherein the resilient sealing member includes a first portion disposed in the socket and contacting the side wall of the socket and a second portion disposed in the socket and spaced from the side wall of the socket; and a stem disposed in the first fitting, including a head, and being axially movable through the socket and the resilient sealing member into the aperture of the second fitting.

2. The connector assembly according to claim 1, wherein the sidewall comprises a continuous cylindrical side wall.

3. The connector assembly according to claim 1, wherein the side wall comprises a distal portion, a proximal portion, and an interior step wherein an interior diameter of the distal portion of the side wall is smaller than an interior diameter of the proximal portion of the side wall.

4. The connector assembly according to claim 1, wherein the resilient sealing member comprises a resiliently compressible and expandable configuration having opposite open ends and an interior passage extending between the opposite open ends.

5. The connector assembly according to claim 1, wherein the second portion comprises a smaller outer diameter than the first portion.

6. The connector assembly according to claim 1, wherein the first portion comprises an inner diameter substantially equal to the inner diameter of the second portion.

7. The connector assembly according to claim 1, wherein the first portion of the resilient sealing member forms a friction fit with the side wall.

8. The connector assembly according to claim 1, wherein the length of the resilient sealing member is greater than the length of the side wall of the socket.

9. The connector assembly according to claim 1, wherein the second portion is resiliently compressible.

10. The connector assembly according to claim 1, wherein the fitting including the socket has a unitary construction.

11. The connector assembly according to claim 1,
   wherein the socket comprises a first socket, the first socket being cooperatively arranged with the first fitting; and
   wherein the resilient sealing member comprises a first resilient sealing member, the first resilient sealing member being disposed in the first socket; and
   wherein the connector assembly further comprises:
      a second socket, wherein the second socket is cooperatively arranged with the second fitting; and
      a second resilient sealing member disposed in the second socket.

12. The connector assembly according to claim 11, wherein the first resilient sealing member and the second resilient sealing member comprise different configurations.

13. A fluid system or device comprising:
   a connector assembly according to claim 1; and
   a fluid container or conduit coupled to one of the first and second fittings.

14. A connector assembly comprising:
   a first fitting including an aperture;
   a second fitting coupleable to the first fitting and having an aperture;
   a socket cooperatively arranged with one of the first and second fittings;
   a resilient sealing member disposed in the socket, wherein the resilient sealing member includes a first portion, a second portion, and a third portion and wherein the second portion is disposed between the first portion and the third portion and has a thinner wall than the first portion and the third portion; and
   a stem disposed in the first fitting, including a head, and being axially moveable through the socket and the resilient sealing member into the aperture of the second fitting.

15. The connector assembly according to claim 14, wherein the socket comprises a continuous cylindrical wall.

16. The connector assembly according to claim 14, wherein the socket comprises an interior step in which the interior diameter of the distal portion of the socket is less than the inner diameter of the proximal portion of the socket.

17. The connector assembly according to claim 14, wherein the resilient sealing member comprises a resiliently compressible and expandable configuration having opposite open ends and an interior passage extending between the opposite open ends.

18. The connector assembly according to claim 14, wherein the second portion comprises an inner diameter equal to the inner diameter of the first portion and the third portion.

19. The connector assembly according to claim 14, wherein the second portion comprises an outer diameter less than the outer diameter of the first portion and the third portion.

20. The connector assembly according to claim 14, wherein the second portion comprises an inner diameter larger than the inner diameter of the first portion and the third portion.

21. The connector assembly according to claim 14, wherein the first portion, the second portion, and the third portion comprises substantially equal outer diameters.

22. The connector assembly according to claim 14, wherein the second portion comprises a compressible configuration.

23. The connector assembly according to claim 14, wherein the first portion is adapted to form a friction fit within the socket.

24. The connector assembly according to claim 14, wherein the length of the resilient sealing member is greater than the length of the socket.

25. The connector assembly according to claim 14, wherein the second portion is disposed in the socket and spaced from the side wall of the socket.

26. The connector assembly according to claim 14, wherein the fitting including the socket has a unitary construction.

27. The connector assembly according to claim 14,
   wherein the socket comprises a first socket, the first socket being cooperatively arranged with the first fitting;
   wherein the resilient sealing member comprises a first resilient sealing member, the first resilient sealing member being disposed in the first socket; and
   wherein the connector assembly further comprises:
      a second socket, wherein the second socket is cooperatively arranged with the second fitting; and
      a second resilient sealing member disposed in the second socket.

28. The connector assembly according to claim 27, wherein the first resilient sealing member and the second resilient sealing member comprise different configurations.

29. A fluid system or device comprising:
   a connector assembly according to claim 14; and
   a fluid container or conduit coupled to one of the first and second fittings.

* * * * *